US011311348B2

(12) United States Patent
Simi et al.

(10) Patent No.: US 11,311,348 B2
(45) Date of Patent: Apr. 26, 2022

(54) ROBOTIC MICROSURGICAL ASSEMBLY

(71) Applicant: MEDICAL MICROINSTRUMENTS S.P.A., Pisa (IT)

(72) Inventors: Massimiliano Simi, Pisa (IT); Giuseppe Maria Prisco, Pisa (IT); Cesare Stefanini, Pisa (IT)

(73) Assignee: MEDICAL MICROINSTRUMENTS S.P.A., Pisa (IT)

( * ) Notice: Subject to any disclaimer, the term of this patent is extended or adjusted under 35 U.S.C. 154(b) by 267 days.

(21) Appl. No.: 16/605,165

(22) PCT Filed: Apr. 16, 2018

(86) PCT No.: PCT/IB2018/052626
§ 371 (c)(1),
(2) Date: Oct. 14, 2019

(87) PCT Pub. No.: WO2018/189729
PCT Pub. Date: Oct. 18, 2018

(65) Prior Publication Data
US 2021/0137618 A1    May 13, 2021

(30) Foreign Application Priority Data

Apr. 14, 2017   (IT) .......................... 102017000042116

(51) Int. Cl.
*A61B 34/37*         (2016.01)
*A61B 34/00*         (2016.01)
(Continued)

(52) U.S. Cl.
CPC .............. *A61B 34/37* (2016.02); *A61B 34/71* (2016.02); *A61B 46/13* (2016.02); *A61B 90/06* (2016.02);
(Continued)

(58) Field of Classification Search
CPC ......... A61B 34/00; A61B 34/37; A61B 34/71; A61B 34/72; A61B 19/201; A61B 19/203;
(Continued)

(56) References Cited

U.S. PATENT DOCUMENTS 5,797,900 A    8/1998   Madhani et al.
6,331,181 B1   12/2001  Tierney et al.
(Continued)

FOREIGN PATENT DOCUMENTS

WO    2010/121117 A1    10/2010
WO    2012/068156 A2    5/2012
(Continued)

OTHER PUBLICATIONS

International Search Report and Written Opinion of the International Searching Authority for International Patent Application No. PCT/IB2018/052626 dated May 23, 2018, 14 pages.

*Primary Examiner* — Vi X Nguyen
(74) *Attorney, Agent, or Firm* — Merchant & Gould P.C.

(57) ABSTRACT

A robotic surgical assembly includes a slave manipulator with an actuator, a pushing device connected to the actuator, a sensor detecting a contact force on the pushing device, a position sensing system, and a control unit. A surgical instrument is detachable to the slave manipulator and separated from the slave manipulator by a sterile barrier. The surgical instrument includes a frame; an articulated link; a tendon associated with the actuator, having proximal and distal portions secured to the link. A transmission device in contact with the tendon proximal portion exerts a traction action. The transmission device has one degree of freedom of motion relative to the frame. The pushing device releasably and selectively connects with the transmission device to transmit a pushing action to the transmission device through (Continued)

the sterile barrier. An elastic device biases the transmission device to exert a traction action on the tendon.

13 Claims, 13 Drawing Sheets

(51) Int. Cl.
*A61B 46/13* (2016.01)
*A61B 90/00* (2016.01)
*A61B 17/00* (2006.01)

(52) U.S. Cl.
CPC .............. *A61B 2017/00477* (2013.01); *A61B 2034/715* (2016.02); *A61B 2090/064* (2016.02)

(58) Field of Classification Search
CPC ..... A61B 19/5244; A61B 46/10; A61B 46/13; A61B 90/00; A61B 90/06

See application file for complete search history.

(56) References Cited

U.S. PATENT DOCUMENTS

| | | |
|---|---|---|
| 6,385,509 B2 | 5/2002 | Das et al. |
| 6,951,535 B2 | 10/2005 | Ghodoussi et al. |
| 6,963,792 B1 | 11/2005 | Green |
| 7,155,316 B2 | 12/2006 | Sutherland et al. |
| 9,173,713 B2 | 11/2015 | Hart et al. |
| 2006/0095022 A1 | 5/2006 | Moll et al. |
| 2007/0137372 A1* | 6/2007 | Devengenzo .......... A61B 34/35 74/490.01 |
| 2009/0036739 A1* | 2/2009 | Hadani ................ A61N 1/0517 600/121 |
| 2012/0071752 A1 | 3/2012 | Sewell et al. |
| 2012/0289974 A1 | 11/2012 | Rogers et al. |
| 2014/0128849 A1 | 5/2014 | Au et al. |
| 2014/0135794 A1 | 5/2014 | Cau |
| 2015/0150636 A1 | 6/2015 | Hagn et al. |
| 2015/0209965 A1 | 7/2015 | Low et al. |

FOREIGN PATENT DOCUMENTS

| | | |
|---|---|---|
| WO | 2015/023730 A1 | 2/2015 |
| WO | 2017/015599 A1 | 1/2017 |

* cited by examiner

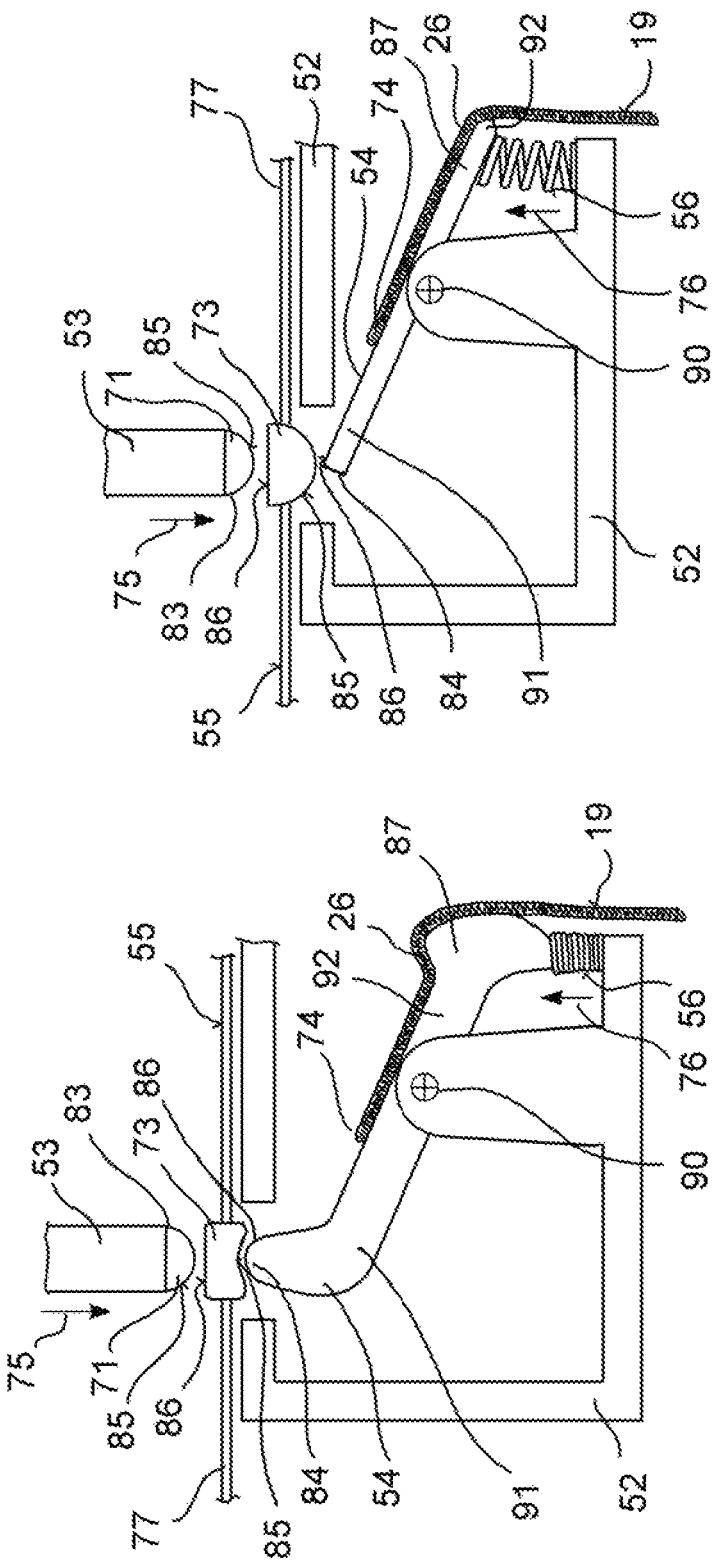

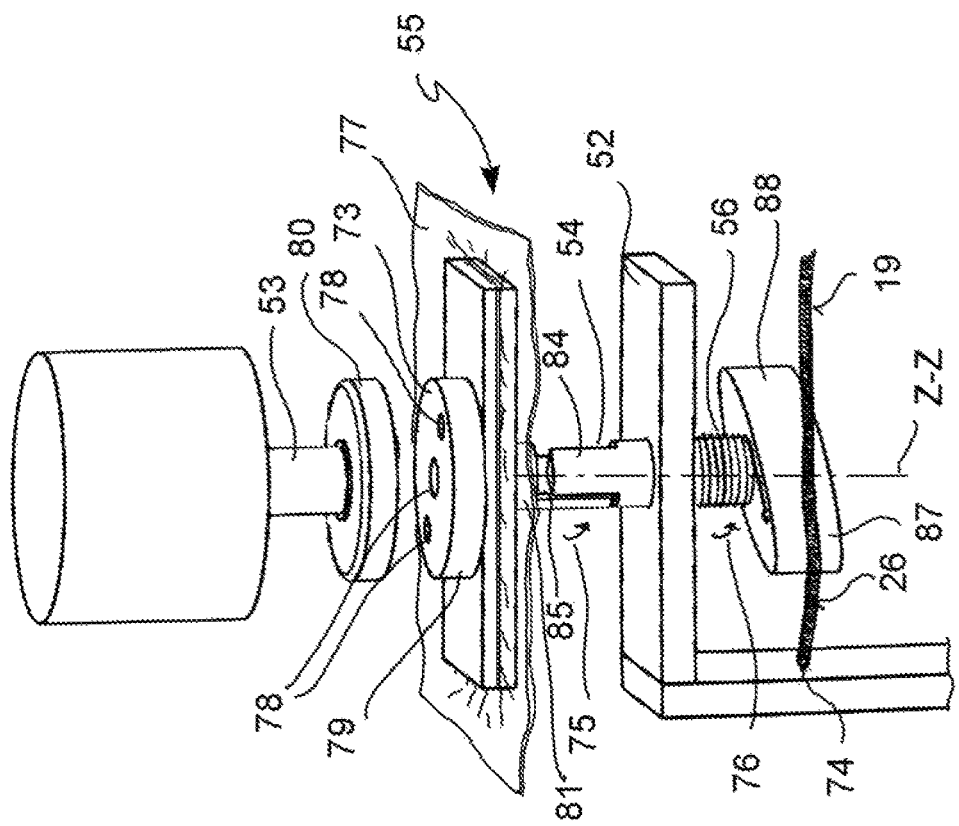
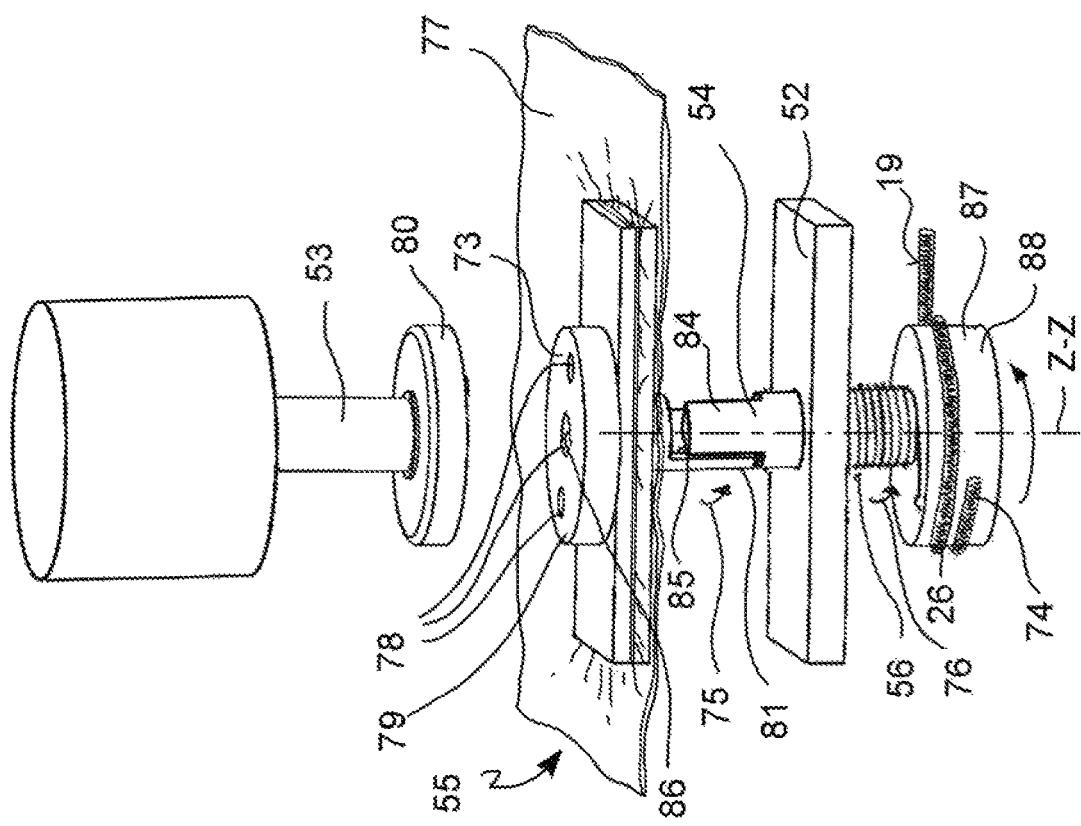

ROBOTIC MICROSURGICAL ASSEMBLY

This application is a National Stage Application of PCT/IB2018/052626, filed 16 Apr. 2018, which claims the benefit of Ser. No. 10/2017000042116, filed 14 Apr. 2017 in Italy, and which applications are incorporated herein by reference. To the extent appropriate, a claim of priority is made to each of the above-disclosed applications.

FILED OF THE INVENTION

It is an object of the present invention a robotic surgical assembly.

The present invention relates to a robotic microsurgical assembly of the type comprising a slave manipulator and a surgical instrument.

The present invention also relates to method for controlling a surgical instrument.

BACKGROUND

Robotic assemblies for surgery or microsurgery comprising multi-joint robotic arms terminating with surgical instruments are known in the field. For instance, document U.S. Pat. No. 7,155,316 discloses a robotic assembly for performing brain microsurgery under Magnetic Resonance Imaging (MRI) guidance comprising an MRI-based image acquisition system and two multi-joint arms, each with three rotary joints with vertical axes to avoid direct gravity loads (as shown for instance in FIG. 7 of said document U.S. Pat. No. 7,155,316), each connected to its respective end-effector endowed with an internal degree of freedom of motion for gripping.

It is also notable that the execution of the principal surgical primitives, such as tissue tensioning and anastomotic suturing, requires the ability to orient the surgical instrument tip in a large spatial cone of directions and to rotate the instrument around its longitudinal axis (roll), for example to guide the needle through the tissue with the tip of the needle holder instrument, in a similar manner as the human hand is jointed at the wrist and the elbow.

Robotic assemblies for surgery or microsurgery comprising a teleoperated master-slave system are generally known, as described, for example, in document U.S. Pat. No. 6,963,792 and, more specifically for the microsurgical application by U.S. Pat. No. 6,385,509, and US-2014-0135794, that describe kinematic solutions for the movement of the surgical instrument tip that require coordination of a plurality of joints in a serial kinematic chain that clutter the operating field. Such encumbrance effect is increasingly pronounced as the joints articulating the tip of the instrument are further away from the tip itself. Moreover said microsurgical systems do not allow adequate movement, and more specifically adequate re-orientation, of the instrument tip when in an operating site inside a lesion as little as 10 centimeters from the surface of the skin.

The adoption of robotic technologies can bring about great benefits, allowing both a high degree of miniaturization of the instruments and scaling the size of the movements in the operating field, hence eliminating the effect of physiological tremor and easing the manual task. For example, microsurgical procedures are carried out in several phases of the reconstruction of biological tissues, such as for example in the execution of blood vessel anastomosis, comprising small diameter vessels, and nerves. Such procedures are carried out to reconstruct anatomy after the occurrence of traumatic lesions or of lesions produced by surgical removal of tissue, to reattach limbs and to revascularized tissues, all performed in an open surgery set-up given the pre-existence of a superficial lesion.

Others examples of application of microsurgical techniques are found in transplant surgery, neurosurgery or in vascular surgery, as well as in surgery around and inside the eye, and in the inner ear, as in the case of cochlear implants. Also the prominent surgical procedure of cardiac by-pass comprises the critical step of anastomosis of the coronary arteries. The need for instrument miniaturization is also felt in other surgical techniques, for example in minimal invasive surgery, such as laparoscopy and endoscopy, that are aimed at limiting the invasiveness of surgical instruments on biological tissue. With reference to laparoscopy, the technical solutions known in the art do not allow a satisfactory miniaturization of the diameter of the laparoscopic instruments employed in Single Incision Laparoscopic Surgery or Single Port Surgery. Moreover, it is worth noticing that the endoscopes typically employed in minimally invasive surgery (MIS) have an instrument channel with a diameter between 1 and 3.2 millimeters. Such dimensions limit the functionality of current surgical instrumentation available through the endoscope instrument channel, which at present is typically just capable of gripping action.

Therefore, it is strongly felt the need to miniaturize surgical instruments for robotic surgery.

Document U.S. Pat. No. 6,951,535 discloses a medical instrument, including an end effector, that mounts on a robotic assembly (FIG. 6). Motion is transmitted to the end effector along the instrument shaft by a rod that can push and pull and a single actuator is bi-directionally engaged with the rod through an adaptor to transmit both a pushing force and a pulling force to the joint. A force sensor senses the force transmitted by the actuator to the rod.

While rods have the advantage over tendons of transmitting both a pushing force and a pulling force and of not requiring tensioning elements, rods have the disadvantage with respect to cable that they cannot be routed through tight bends and through tightly bending joints such as tendons can, so that the proposed approach is not suitable for actuation of a miniature jointed subassembly such as a wrist.

For example, U.S. Pat. No. 9,173,713 discloses a medical instrument, specifically a catheter, actuated by pull wires and includes a tension sensor to control the force applied by the actuators to the pull wires. Pull wires routed into lumens of the catheter have the advantage with respect to tendons of not requiring tensioning elements. On the other hand, pull wires cannot be routed through tight bends and through tightly bending joints such as tendons can, so that the proposed approach is not suitable for actuation of a miniature jointed subassembly such as a wrist.

Moreover, U.S. Pat. No. 5,797,900 discloses in FIG. 6 and FIG. 7 a cable drive system of a surgical instrument. It includes an actuator directly acting on the cable by a friction drive composed of a capstan or a drive wheel. The cable passes over a rear tensioning pulley that provides a cable pretension. The actuator acting directly on the cable via a friction drive does not allow the detachment of the instrument from the actuator nor the introduction of a sterile barrier between actuator and instrument. Moreover a friction drive has the disadvantage to allow always some slippage between the actuator and the cable. Slippage negatively affects the ability to control precisely the position of the distal articulation of the surgical instrument, even more so when the surgical instrument has a small diameter, e.g. below 5 mm.

Document U.S. Pat. No. 6,331,181 discloses a robotic surgical instrument including a sterile drape and a sterile adaptor and a surgical instrument including jointed distal articulation that is actuated by tendons. The document describes a tendon drive system in FIG. 4B without any tendon tensioning device. This approach has the disadvantage that it cannot eliminate lost motion between the actuator and the distal joint that appears whenever a tendon in the instrument looses its pretension or preload. The loss of pretension is significant for steel cables and is even more pronounced over the life of the instrument for tendons that stretch or creep over time under tension, such as for example polymeric cables. This effect can be mitigated by applying a large pretension to the tendons when the instrument is assembled, but a large pretension in turn increases the friction in the jointed distal articulation and impairs its motion precision, especially if the instrument distal articulation has small dimensions. In conclusion, the disclosed approach is not suitable to actuate a microinstrument with a distal articulation with a diameter less than 5 millimeters or instruments that use polymeric tendons.

The International patent application WO-2012-068156 discloses a tendon drive system for a medical instrument that includes a differential mechanism by device of tendons and moving pulleys. The proposed solution lacks device to pick up tendon slack or provide tension to the tendons and it cannot eliminate lost motion between the actuator and the distal joint that appears whenever a tendon in the instrument looses its pretension.

Document US-2015-0209965 discloses a tendon driven medical instrument including jointed distal articulation. A robotic assembly includes an actuator pack. The instrument includes a coupling unit which connects to the actuator pack. Said coupling unit of said instrument includes sensors that sense the tension of the tendons. Said coupling unit of said instrument also includes spools attached to the motor shaft that can take up slack in the cable when the instrument is mounted on the robotic assembly. The proposed solution has the disadvantage of locating said tension sensors inside the instrument coupling unit increasing the cost of a component that could be disposable. When the instrument is detached from the actuators, no device of pretensioning the tendons and pick up slack in the tendons are provided. Such solution cannot be adopted in tendon drive systems that require a pick up of slack in the tendons for proper functioning, such as for example in case of tendons that are prone to creep or stretch under load.

In addition, WO-2017-015599 discloses a tendon-driven medical instrument including jointed distal articulation. The instrument presents transmission device adapted to transmit force from the actuator to the tendons that include an input finger on which the actuator engages unidirectionally. The proposed unidirectional engagement has the advantage of allowing a simple sterile barrier in the form of a continuous sheet with bellows that cover the input fingers. On the other hand, no device of pre-tensioning the tendons and pick up slack in the tendons when the instrument is detached from the actuators are described. Such solution cannot be adopted in tendon drive systems that require a minimum preload in the tendons for proper functioning, such as for example in case of tendons that are prone to creep or stretch under load.

US-2014-0128849 discloses a variety of tendon drive systems of a medical instrument that include a friction drive composed of a capstan that transmit force to the tendon by virtue of friction. An engagement mechanism between the actuator and the capstan is described to allow removal of the instrument and to keep the actuator outside of a sterile area via sterile barrier. A number of solution to provide pretension to the tendon when the instrument is not attached to the actuators are all based on spring elements connected between the instrument frame and the tendon or to pretensioning pulleys on which the tendon is routed. In one embodiment shown therein, tendon take up spring systems are required, thus increasing compliance in the transmission, and reducing the instrument motion precision. In any case, the friction drive has the disadvantage to allow always some slippage between the actuator and the cable that negatively affects the ability to control precisely the position of the distal articulation of the surgical instrument.

Document US-2012-0289974 discloses an instrument actuation interface for a surgical instrument in which a portion of the drive element, a tendon or a rod, is exposed to direct movement by a manipulator across a sterile barrier. Despite its simplicity, the proposed solution has the fundamental disadvantage of directly trapping the sterile barrier, for example a plastic sheet, between the manipulator and the tendon, exposing the sterile barrier and the tendon to wear or mechanical failures as a result of their direct mechanical interaction during their relative motion. In alternative embodiments, pinion gears, gear racks or drive friction rollers or other adaptors are included in the sterile barrier to transmit motion from the actuator to the drive element. Such solutions fail to provide any amount of the required pretension or take up to a tendon type drive device when the instrument is not attached to the actuator and so they cannot be adopted in tendon drive systems that require a minimum preload in the tendons for proper functioning.

Furthermore, US-2015-0150636 discloses a medical instrument with a transmission device that can deflect a tendon from its path when acted on by a human in one direction. No tendon tensioning element to pick up tendon slack is provided in the instrument. To the opposite effect, a return spring is provided to keep transmission device away from the tendon when transmission device in not acted on by a human.

Furthermore WO-2010-121117 discloses a drive system for a surgical instruments including a piston as pushing means and a plunger as transmission means and a spring as elastic means. In the disclosed solution, the spring drives the opening of a distal degree of freedom and moves the plunger rearwards towards the piston, keeping it in contact with the plunger at all times during normal operation. Thus the spring is used to actuate an opening motion while the plunger is used to actuate a closing motion of the same degree of freedom. The use of a spring to actuate a motion in one direction of a degree of freedom has the disadvantage of limiting the degree of control of the motion in said direction, in other words the motion in said direction is controlled passively by the spring and not actively controlled, in the way it is controlled by an actuator driving pushing means. As a consequence, the force and the speed is said direction are not actively controllable to perform exact surgical gestures.

Document WO-2015-023730 discloses a surgical device including a motorbox and a surgical instruments including a tendon with a distal portion connected to a distal joint and a proximal portion connected to a drive disk that acts as bidirectional transmission means for said distal joint. This document discloses a solution, based on a preload mechanism build in on the motor side, of how to engage said drive disk onto said motor pack to transmit motion bi-directionally without incurring in backlash or lost motion. The proposed preload mechanism does not affect the tension in the tendon, but only enforces the contact between the drive disk and the motor. Thus the tension in the tendon in the instruments needs to be set to a value high enough to guarantee no slack of the tendon in any operating condition, which tends to increase the friction in the instrument and reduce its motion precision.

Therefore, it is felt the need to provide a tendon drive system for a medical instrument including a distal articulated subassembly, that includes a tendon pretensioning element that is part of the medical instrument.

It is felt the need, when the medical instruments are not mounted on the robotic assembly, that a tendon has always a minimal positive tension (preload) for any position of the distal articulated subassembly.

In fact, slack in the tendons, can also result from tendons slippage over routing elements. Then, slack in tendons can result from the application over the life of the instrument of a pretension. Slack in the tendons can result from tendons that tend to stretch or creep over time when under a tension load.

It is felt the need to provide a tendon drive system for a medical instrument including a distal articulated subassembly that applies a pretension to a tendon that, when the instrument is detached from the actuator, is lower than the tension applied to the tendon during normal operations, as a lower pretension in a tendon beneficial for the life of the tendon.

It is felt the need to provide a tendon drive system for a medical instrument including a distal articulated subassembly that comprises a transmission device that is adapted to transmit forces from an actuator of a slave manipulator to said tendon without damaging the tendon.

At the same time, it is felt the need in a master-slave system for driving a medical instrument to provide a sterile barrier between the medical instrument and the slave manipulator, so that the medical instrument can be sterile and the slave manipulator avoids contaminating it.

SOLUTION

A scope of the invention described here is to overcome the limitations of known solutions as described above and to provide a solution to the needs mentioned with reference to the state of the art.

According to an aspect of the invention, a robotic surgical assembly comprises a slave manipulator comprising an actuator, at least one pushing device, connected to said actuator, at least one sensor, detecting a contact force on said pushing device, a position sensing system, a sterile barrier, at least one control unit configured to receive information about said sensor to control said actuator; and at least one surgical instrument operated on by said slave manipulator and detachably attached to said slave manipulator and separated from said slave manipulator by said sterile barrier.

According to an aspect of the invention, said surgical instrument further comprises a frame, a link articulating in a joint with respect to said frame, a tendon, associated to said actuator, having a tendon proximal portion, and a tendon distal portion, secured to said link, at least one transmission device, in contact with said tendon proximal portion, in order to exert a traction action on said tendon; said transmission device being constrained by a coupling device to have a single degree of freedom of motion with respect to said frame, at least one elastic device attached between said transmission device and said instrument frame.

According to a preferred embodiment, whenever said surgical instrument is attached to said slave manipulator, said at least one pushing device releasably and selectively connects with said transmission device to transmit a pushing action to said transmission device through said sterile barrier, and said at least one sensor detects a contact force between said pushing device and said transmission device, and said at least one elastic device bias said at least one transmission device away from said pushing device, so as to exert a traction action on said tendon.

Thanks to the proposed solutions, slack in tendons is avoided.

According to a preferred embodiment, said slave manipulator comprises: at least a second pushing device working as antagonist pushing device, at least a second actuator connected to said antagonist pushing device, at least second transmission device working as antagonist transmission device, a second force sensor, and wherein said surgical instrument comprises at least a second tendon working as antagonist tendons and a second elastic device, attached to said second transmission device wherein, whenever said surgical instrument is attached to said slave manipulator, said antagonist pushing device releasably and selectively connects with said antagonist transmission device to transmit a pushing action to said antagonist transmission device through said sterile barrier; said second sensor detects a contact force between said antagonist pushing device and said antagonist transmission device; said antagonist elastic device bias said antagonist transmission device away from said antagonist pushing device, so as to exert a traction action on said antagonist tendon; said tendon and said antagonist tendon provide opposite motion to a link.

Thanks to the proposed solutions, it is allowed in a master-slave system for driving a medical instrument, to provide active control of the common tendon tension in a pair of tendons distally attached to a joint in an antagonist configuration.

Thanks to the proposed solutions, it is allowed, in a master-slave system for driving a medical instrument, to disconnect a tendon actuator from the instrument while the instrument is engaged on the master-slave system, so that the tension in the tendon is this reduced to its minimum value required to avoid slack in the tendon.

FIGURES

Further characteristics and advantages of the invention will appear from the description reported below of preferred embodiments, which are given as examples and are not meant to be limiting, which makes reference to the attached figures, in which:

FIGS. 17 and 18 are sketches in cross-section of a of a surgical instrument and of a slave manipulator, according to some embodiments;

FIGS. 19 and 20 are sketches in cross-section of a of a surgical instrument and of a slave manipulator, according to some embodiments;

DETAILED DESCRIPTION OF SOME PREFERRED EMBODIMENTS

Figure 1:
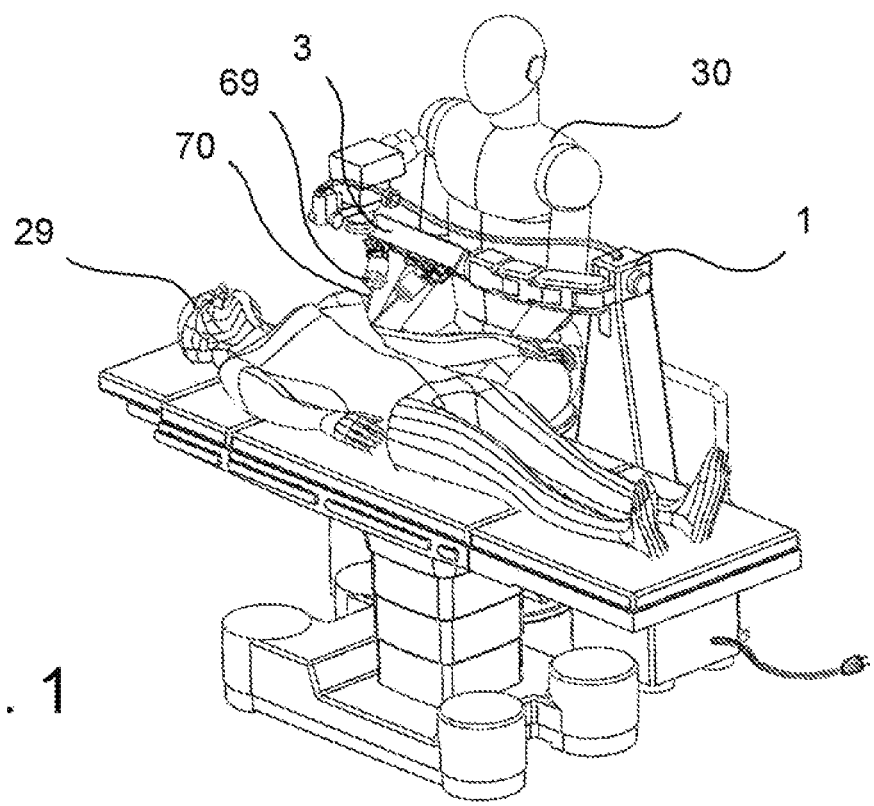
FIG. 1 is a perspective view of a robotic surgical assembly, according to an embodiment, wherein sketches depict a patient a surgeon.
Figure 2:
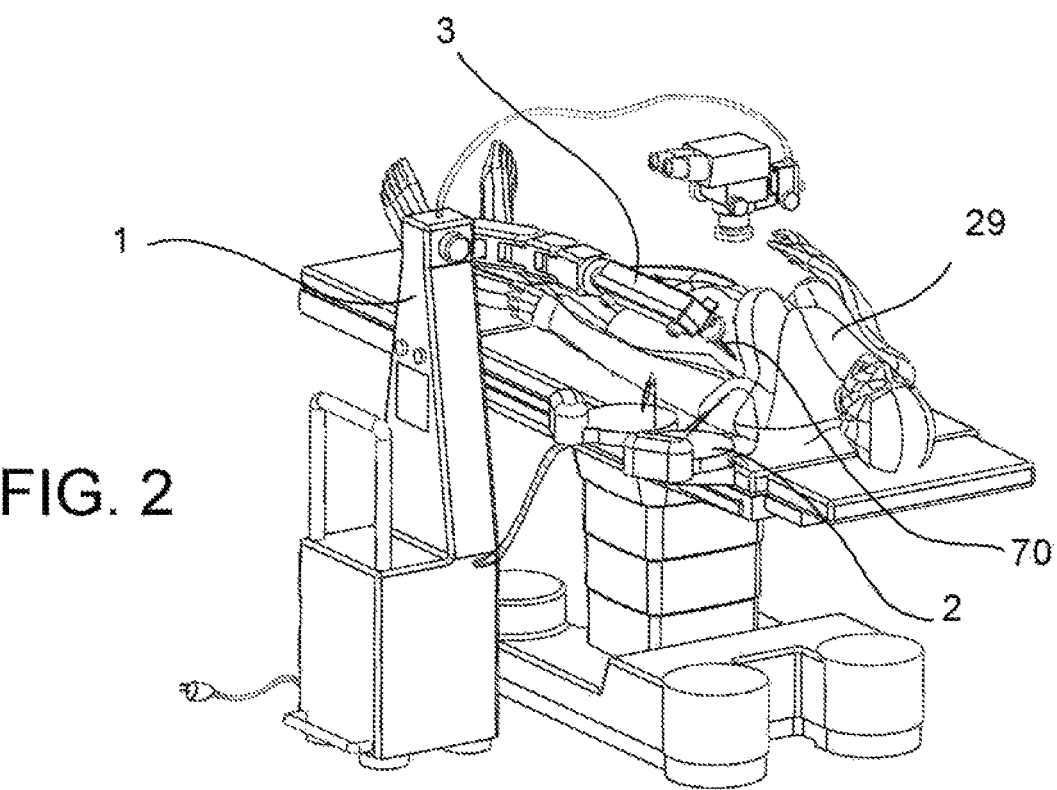
FIG. 2 is a perspective view of a robotic surgical assembly, according to an embodiment, wherein a sketch depicts a patient.
Figure 3A:
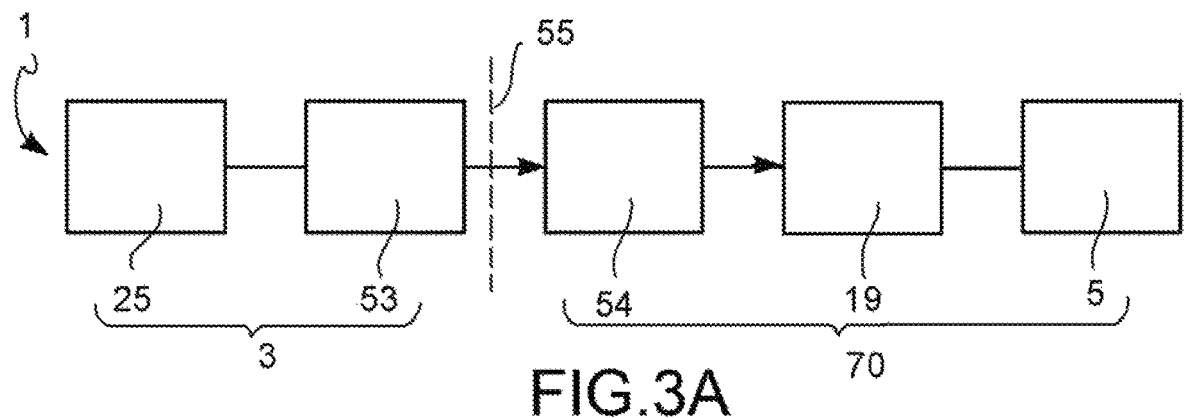
FIG. 3A is a block diagram of a slave assembly of a robotic surgical assembly, according to an embodiment.
Figure 3B:
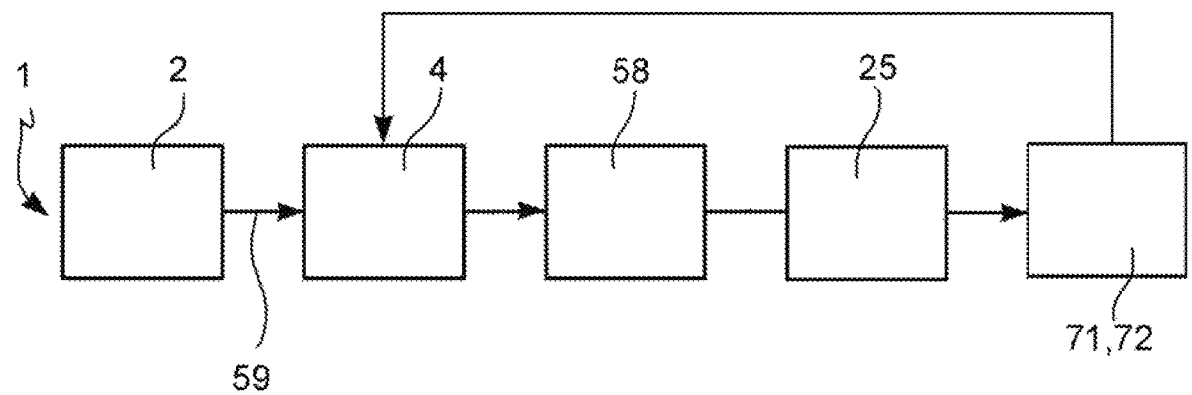
FIG. 3B is a block diagram of a robotic surgical assembly, according to an embodiment.
Figure 3C:
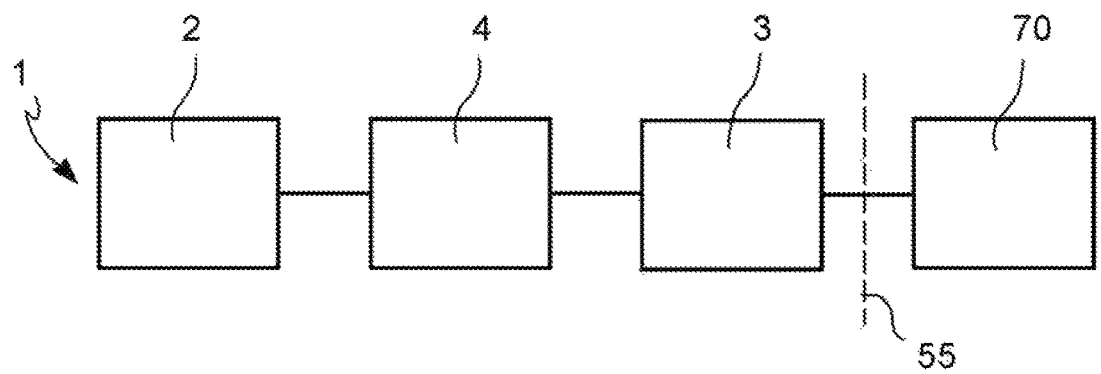
FIG. 3C is a block diagram of a robotic surgical assembly, according to an embodiment.
Figure 4:
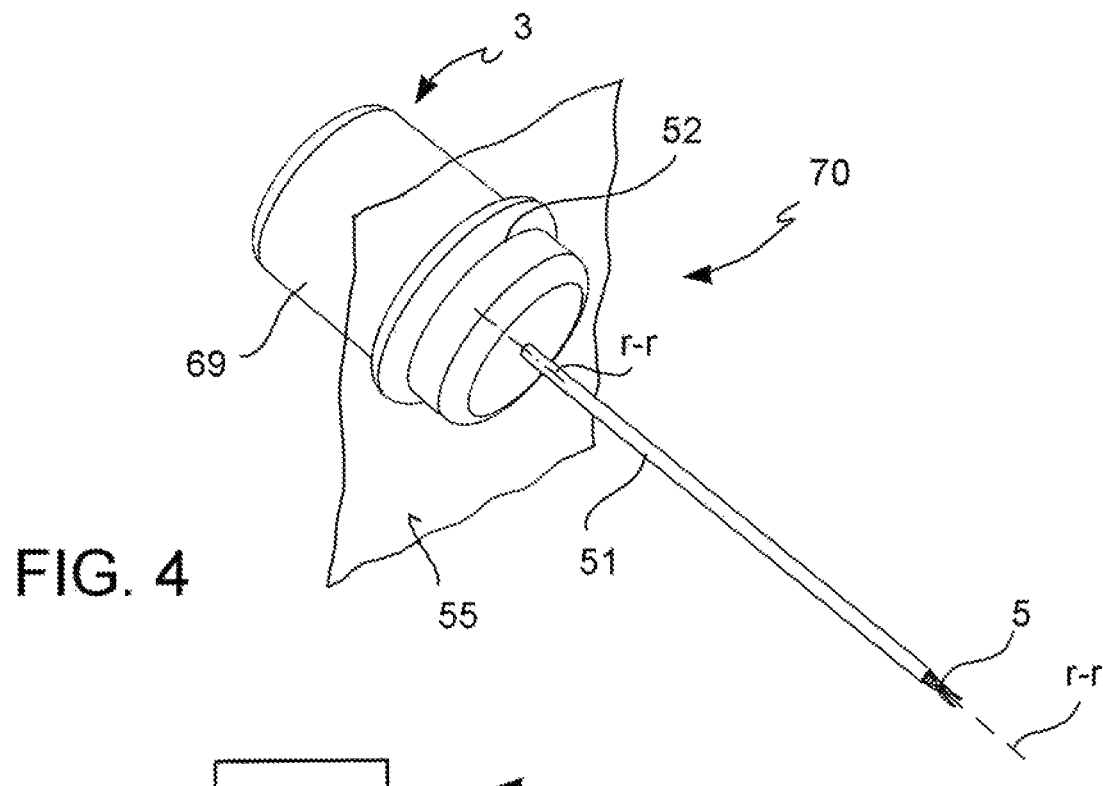
FIG. 4 is a perspective view of surgical instrument and of a slave manipulator, according to an embodiment.
Figure 5:
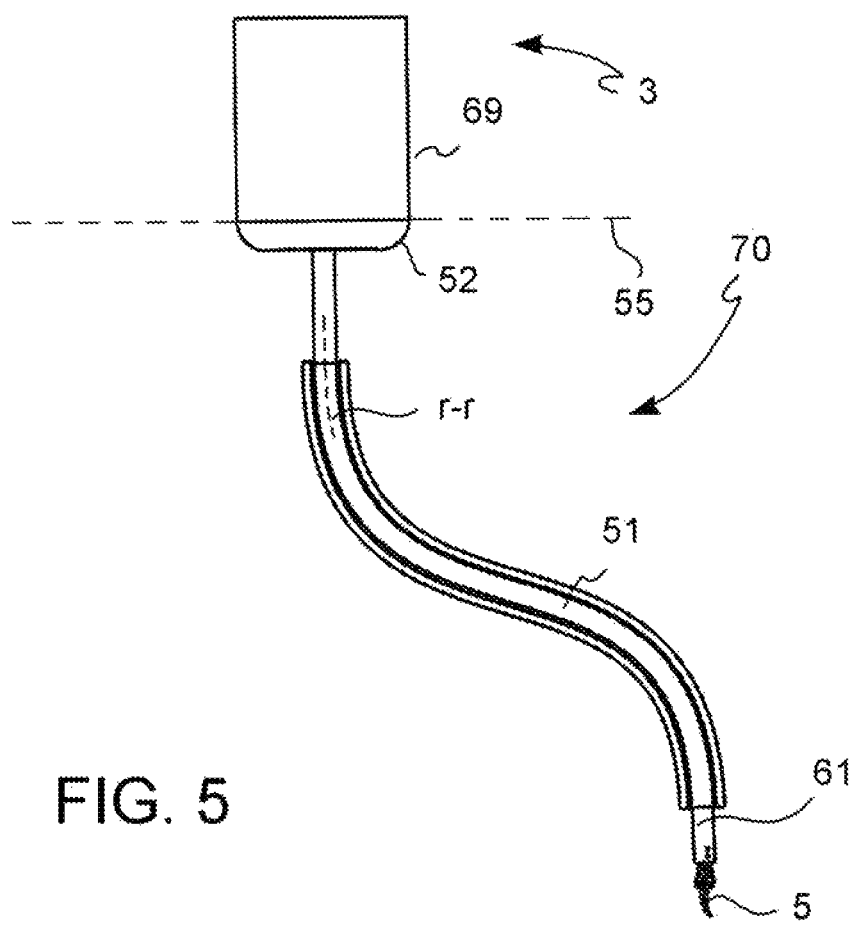
FIG. 5 is a plan view of a surgical instrument and of a slave manipulator, according to an embodiment.

According to a general embodiment, it is provided a robotic surgical assembly 1.

Said robotic surgical assembly 1 comprises a slave manipulator 3.

Said slave manipulator 3 comprises an actuator 25, at least one pushing device 53 connected to said actuator 25, a sensor 71, 72 detecting a contact force on said at least one pushing device 53, a position sensing system 72, a sterile barrier 55, at least one control unit 4 configured to receive information about said sensor to control said actuator 25, and a surgical instrument 70.

According to a preferred embodiment, said surgical instrument 70 is operated on by said slave manipulator 3 and detachably attached to said slave manipulator 3 and separated from said slave manipulator 3 by said sterile barrier 55.

Said surgical instrument 70 further comprises a frame 52, a link 6; 7; 8; 43 articulating in a joint 14; 17 with respect to said frame 52, a tendon 19, associated to said actuator 25, having a tendon proximal portion 26, and a tendon distal portion 27, secured to said link 6; 7; 8; 43.

Said surgical instrument 70 further comprises at least one transmission device 54, in contact with said tendon proximal portion 26, in order to exert a traction action on said tendon 19.

Said at least one transmission device 54 is constrained by at least one coupling device 93 to have a single degree of freedom of motion with respect to said frame 52. Preferably, said coupling device 93 is a linear coupling device 93. For example, said coupling device 93 is a wall of the frame 52.

Said surgical instrument 70 further comprises at least one elastic device 56 attached to said at least one transmission device 54.

Preferably, said pushing device 53 releasably and selectively connects with said transmission device 54 to transmit a pushing action to said transmission device 54 trough said sterile barrier 55. According to a preferred embodiment, whenever said surgical instrument 70 is attached to said slave manipulator, said pushing device 53 being releasably and selectively connected with said transmission device 54 to transmit a pushing action to said transmission device 54 through said sterile barrier 55, said sensor 71, 72 detects a contact force between said pushing device 53 and said transmission device 54, said elastic device 53 biases said transmission device 54 away from said pushing device 53, so as to exert a traction action on said tendon 19. According to a preferred embodiment, said elastic device 53 is attached between said instrument frame 52 and said transmission device 54. According to a preferred embodiment, said elastic device 53 acts as a compliance between said instrument frame 52 and said transmission device 54. According to a preferred embodiment, said elastic device 53 generates a said bias action 76, between said instrument frame 52 and said transmission device 54. According to a preferred embodiment, said bias action 76 bias said transmission device 54 away from said pushing device 53. According to a preferred embodiment, said bias action 76 exert a traction action on said tendon 19.

According to a preferred embodiment, said pushing device 53 is selectively connected with said transmission device 54 to transmit said pushing action 75 by means of a unilateral engagement with said sterile barrier and said transmission device 54. According to a preferred embodiment, said pushing device 53 is selectively connected with said transmission device 54 to transmit said pushing action 75 by means of a unilateral rigid engagement with said sterile barrier and said transmission device 54. According to a preferred embodiment, said pushing device 53 are not detained by said transmission device 54 nor by said sterile barrier. According to a preferred embodiment said pushing device 53 acts on said transmission device 54 through said sterile barrier, in parallel with said elastic device 53. In this way, said elastic device 53 avoids to add compliance in series with said pushing device, in the transmission of pushing action 75 between said pushing device and said tendon 19.

According to a preferred embodiment, said sterile barrier 55 comprises a stretchable sterile drape 77 and when said pushing device 53 connects to said transmission device 54 to transmit said pushing action 75 a portion of said stretchable sterile drape 77 is trapped between said pushing device 53 and said transmission device 54.

According to a preferred embodiment, wherein said sterile barrier 55 comprises a stretchable sterile drape 77 and a sterile drape insert 73, attached to said drape 77, wherein when said pushing device 53 connects to said transmission device 54 to transmit said pushing action 75, said sterile drape insert 73 is trapped between said pushing device 53 and said transmission device 54. According to an embodiment, said sterile drape insert 73 is a sterile barrier connector.

According to a preferred embodiment, said coupling device 93 constrains one of said transmission device 54 to have a single degree of freedom of linear motion with respect to said frame 52. According to a preferred embodiment, said at least one coupling device 93 constrains at least one of said transmission device 54 to have a single degree of freedom of linear motion with respect to said frame 52.

According to a preferred embodiment, said elastic device 56 comprise an axial spring. According to an embodiment, said axial spring is a linear compression coil spring. According to an embodiment, said axial spring is a linear traction coil spring.

According to a preferred embodiment, said coupling device 93 constrain said transmission device 54 to have a single degree of freedom of pivotal motion with respect to said frame 52.

According to a preferred embodiment, said elastic device 56 comprise a torsion spring. According to an embodiment, said torsion spring is a coil spring. According to an embodiment, said torsion spring is a rotary spring. According to an embodiment, said at least one tensioning element 56 is an axial spring. According to an embodiment, said at least one tensioning element 56 is a coil axial compression spring. According to an embodiment, said at least one tensioning element 56 is a coil axial tension spring.

According to an embodiment, said at least one tensioning element 56 is a torsion spring.

According to a preferred embodiment, said at least one transmission device 54 comprises at least one of a cam surface, ball bearing, a lever 54 pivotally connected to said frame 52, a plunger 54, a tendon attachment surface.

According to a preferred embodiment, said elastic device 56 and/or said coupling device comprises a plurality of flexural elements 89, extending from said frame 52 to said transmission device 54.

According to a preferred embodiment, a robotic surgical assembly 1 comprises at least one master tool 2, suitable to detect a manual command, at least one slave manipulator 3, at least one surgical instrument 70 operated on by said one slave manipulator 3, and at least one control unit 4 configured to receive at least a first command signal 59 comprising information about said manual command and to send a second command signal 60 to at least one actuator 25 to control said slave manipulator 3.

According to an embodiment, said control unit 4 is connected to an actuator drive unit 58, suitable for send said second command signal to said at least one actuator 25. According to an embodiment, said at least one control unit 4 comprises a CPU. According to an embodiment, said at least one control unit 4 comprises at least one processor unit. According to an embodiment, said at least one control unit 4 provides a feedback control circuit based on the information acquired by a detection system suitable for detecting the action, for example the displacement provided and/or the force exerted by, of said at least one actuator 25. According to an embodiment, said master tool 2 is designed to be handled by a surgeon 30. According to an embodiment, at least a portion of said surgical instrument 70 is designed to operate on the anatomy of a patient 29.

According to an embodiment, said surgical instrument 70 comprises a frame 52 and at least one jointed subassembly 5, kinematically associated with said frame 52.

According to an embodiment, said jointed subassembly 5 comprises links 6, 7, 8, 43 connected by joints 14, 17, defining a plurality of degrees of freedom. According to an embodiment, a shaft 51 is proximally connected to said frame 52 and distally connected to a link of said jointed subassembly 5, forming a tubular element connection 61. According to an embodiment, said shaft 51 defines a longitudinal shaft axis r-r, substantially coincident to the axis of longitudinal development of said shaft 51. According to an embodiment, said shaft 51 is suitable to rotate around said longitudinal shaft axis r-r to provide a roll motion to the jointed subassembly.

According to an embodiment, said surgical instrument 70 comprises at least one tendon 19, directly or indirectly associated to said at least one actuator 25, suitable for working as an actuation cable. According to a preferred embodiment, said at least one tendon 19 has a tendon proximal portion 26, and a tendon distal portion 27, secured to one of said links 6, 7, 8, 43. Preferably, said at least one tendon 19 comprises a tendon intermediate portion 28, extending between said tendon proximal portion 26 and said tendon distal portion 27. According to a preferred embodiment, said tendon 19 comprises a tendon proximal termination 74 secured to said frame 52. According to a preferred embodiment, said tendon proximal termination 74 is glued to said frame 52.

According to an embodiment, said slave manipulator 3 comprises pushing device 53, connected to said at least one actuator 25. Preferably, said pushing device 53 comprises at least one pushing element 53. According to an embodiment, said pushing device 53 or at least one pushing element 53, are connected to said at least one actuator 25.

According to an embodiment, said surgical instrument 70 comprises transmission device 54 in contact with said tendon proximal portion 26, in order to exert a traction action on said tendon 19. Preferably, said transmission device 54 comprise at least one transmission element 54. According to an embodiment, said at least one transmission element 54, or transmission device 54, comprises a tendon contacting portion 87 in contact with said tendon proximal portion 26. According to a preferred embodiment, said tendon proximal termination 74 is secured to said transmission device 54.

According to an embodiment, when in use, said at least one pushing element 53 is selectively connected with said at least one transmission element 54 to transmit a pushing action 75 to said transmission element 54. Preferably, said at least one pushing element 53 is releasably and selectively connected with said at least one transmission element 54. According to an embodiment, said at least one pushing element 53 releasably rests against said transmission element 54.

According to an embodiment, in a given time instant when in use, said at least one pushing element 53 can be either connected with or disconnected from said at least one transmission element 54.

According to an embodiment, when in use, said at least one pushing element 53, or pushing device 53, is selectively in direct or indirect contact with said at least one transmission device 54 to transmit a pushing action to said transmission device 54.

According to an embodiment, said robotic surgical assembly 1 comprises a sterile barrier 55, at least a portion of said sterile barrier 55 being interposed between said at least pushing element 53 and said at least one transmission element 54. In this way, the selective contact between said pushing device 53 and said transmission device 54 is indirect, as the sterile barrier 55 is disposed between said pushing device 53 and said transmission device 54. Thanks to said sterile barrier 55, it is possible to avoid mutual bacterial contamination across said sterile barrier 55, therefore defining a sterile surgical instrument 70 and a non-sterile slave manipulator 3.

According to an embodiment, said transmission device 54 being associated to said frame 53 by device of a coupling device, said coupling device constraining said transmission device 54 to have a single degree of freedom of motion with respect to said frame 52. According to an embodiment, when said surgical instrument 70 is detachably attached to said slave manipulator 3 and in use, said pushing device 53 are selectively in contact with said transmission device 54 to transmit a pushing action to said transmission device 54 through said sterile barrier 55.

According to an embodiment, said at least one pushing element 53 comprises at least an output portion 83 and said at least one transmission element 54 comprises at least one input portion 84, said output portion 83 directly or indirectly through said sterile barrier 55 transmitting said pushing action 75 to said input portion 84.

According to an embodiment, said surgical instrument 70 comprises elastic device 56 associated to said transmission device 54 to bias said transmission device 54 away from said pushing device 53, to exert a traction action on said tendon 19. Preferably, said elastic device 56 comprise at least an elastic element like a spring or the like.

According to an embodiment, said traction action on said tendon is an elastic traction action on said tendon. In this way.

According to a preferred embodiment, said elastic device 56 comprise at least a spring 56. According to a preferred embodiment, said elastic device 56 comprise at least a coil spring 56. According to a preferred embodiment, said at least one elastic mean 56 comprises at least a leaf spring 56.

According to an embodiment, said elastic device 56 exert a bias action 76 on said transmission device 54 to exert a traction action on said tendon 19. Preferably, said bias action 76 is an elastic bias action 76.

According to a preferred embodiment, said slave manipulator 3 comprises at least one sensor 71, 72 detecting the contact force between said pushing device 53 and said transmission device 54. According to an embodiment, said pushing action 75 of said pushing device 53 and said bias action 76 provided by said elastic device 56 act in the same line and with the same direction.

According to a preferred embodiment, said slave manipulator 3 comprises at least a position sensing system 72 capable of detecting said actuator position and detecting the stroke of said pushing device 53.

According to an embodiment, said at least one sensor 71 is a load cell. According to an embodiment, said at least one sensor 71 comprises a piezoelectric device. According to a preferred embodiment, said at least one sensor 71 is a pressure sensor. According to a preferred embodiment, said at least one sensor 71 is a resistive, thin film pressure sensor.

According to an embodiment, said at least one position sensing system 72 includes an encoder. According to an embodiment, said at least one position sensing system 72 includes a linear encoder. According to an embodiment, at least said at least one position sensing system 72 includes a rotative encoder. According to an embodiment, said at least said at least one position sensing system 72 includes a limit switch. According to an embodiment, said at least said at least one position sensing system 72 includes a processor memory register accumulating incremental actuator position commands. According to a preferred embodiment, said at least said at least one position sensing system 72 includes an absolute position encoder.

According to an embodiment, said at least one position sensing system 72 detects the gap value between said at least pushing device 53 and said at least one transmission device 54.

According to an embodiment, when the contact force between said pushing device 53 and said transmission device 54 is equal to or greater than a predefined contact force threshold value, said at least one sensor 71 sends a sensor signal to said control unit 4. In this way, it is avoided that the detection noise can trigger said actuator 25.

According to an embodiment, when the gap value between said at least pushing device 53 and said at least one transmission device 54 is equal to or lower that a predetermined distance value, said at least one position sensing system 72 sends a position sensing system signal to said control unit 4. In this way, it is possible to feedback control said actuator 25.

According to an embodiment, said sensor 71 and said position sensing system 72 cooperate to determine the extent of the free stroke of said pushing device 53 in respect of a reference position of said pushing device 53, i.e. actuator 25. According to an embodiment, said free stroke is a portion of the stroke of said pushing device 53 in which said pushing device 53 are free from connection with said transmission device 54.

According to an embodiment, said at least one sensor 71, 72 is a LVDT. According to an embodiment, said LVDT is placed on said pushing device 53 detecting the gap value between said pushing device 53 and said transmission device 54. According to an embodiment, said at least one sensor 71, 72 is an Eddy current proximity sensor.

According to an embodiment, said at elastic device 56 elastically biases said transmission device 54 to exert a traction action on said tendon 19.

According to an embodiment, said elastic device 56 elastically bias said transmission device 54 to provide a preload to said tendon 19. According to an embodiment, said elastic device 56 elastically bias said transmission device 54 to provide said tendon intermediate portion 28 with a preload. In this way, said at least one tendon 19, preferably said tendon intermediate portion 28 of said tendon 19, is preloaded, when in use. Preferably, said at least one tendon 19, preferably said tendon intermediate portion 28 of said tendon 19, is constantly and slightly preloaded, when in use. In this way, a minimum pushing action exerted by said pushing device 53 on said transmission device 54 determines a traction action on said tendon 19, preferably on said tendon proximal portion 26.

According to an embodiment, said at least one elastic device 56 is formed of a soft spring.

According to an embodiment, said the contact force between said pushing device 53 and said transmission device 54 adds to the bias action 76 provided by said elastic device 56. According to an embodiment, the pushing action 75 transmitted from said pushing device 53 to said transmission device 54 add to the bias action 76 provided by said tensioning element 56.

According to an embodiment, said at least one tensioning element 56 is connected in parallel with said one transmission device 54.

According to an embodiment, said at least one tensioning element 56 biases said transmission device 54 away from said pushing device 53.

According to an embodiment, said sterile barrier 55 comprises a stretchable sterile drape 77.

According to an embodiment, said sterile barrier 55 comprises a sterile drape insert 73.

According to an embodiment, said sterile drape insert 73 transmits the pushing action 76 exerted by said pushing device 53 to said transmission device 54.

According to an embodiment, said sterile drape insert 73 acts as a transmission device.

According to an embodiment, said sterile drape is stretchable and said sterile drape insert 73 is a rigid body. In this way it is possible to transmit the pushing action 76 avoiding to damp or dim said pushing action 76.

According to an embodiment, said sterile drape insert 73 comprises at least a drape attachment device to connect with said drape 77. According to an embodiment, said sterile drape insert 73 switches a portion of said drape 77.

According to a preferred embodiment, said surgical instrument 70 is detachably associated to said slave manipulator 3. According to an embodiment, said surgical instrument 70 is detachably associated to said slave manipulator 3 through said at least one sterile barrier 55. According to an embodiment, said surgical instrument 70 is detachably associated to said at least one sterile drape insert 73. According to an embodiment, said at least one sterile drape insert 73 is detachably associated to said slave manipulator 3.

According to an embodiment, said tendon contacting portion 87 of said transmission device 54 selectively deflect said tendon proximal portion 26. According to an embodiment, said tendon contacting portion 87 of said at least one transmission device 54 deflects said tendon proximal portion 26 when said at transmission device 54 transmit a pushing action 75 to said transmission device 54.

According to an embodiment, said transmission device 54 urges said tendon proximal portion 26 transversally, so as to generate a traction action onto said intermediate portion of said tendon. According to an embodiment, said tendon contacting portion 87 of said transmission device 54 pushes said tendon proximal portion 26 in a direction transverse to the local longitudinal development of said tendon 19, so that such a transversally-directed action applied to said tendon by said pushing device through said transmission device 54, generates a traction action onto at least said intermediate portion of said tendon.

According to an embodiment, said tendon contacting portion 87 of said at least one transmission device 54 comprise a pulley being in contact with said tendon proximal portion 26. Preferably, said pulley is pivotally associated with said transmission device 54.

According to an embodiment, said at least one transmission element 54 is in single piece. According to a preferred embodiment, the terminology "single piece" indicates that any degree of freedom is avoided within said transmission element 54.

According to an embodiment, said transmission device 54 comprise at least one plunger 54. Preferably, said coupling device constrains said plunger 54 to have a single degree of freedom of linear motion with respect to said frame 52.

According to an embodiment, said transmission device 54 comprise at least one lever 54 pivotally connected to said frame 52. In this way, said lever acts as coupling device 93 constraining said transmission device 54 or lever 54 to have a single degree of freedom of motion with respect to said frame 52.

Preferably, said lever 54 pivotally connected to said frame 52 in a fulcrum joint 90. According to an embodiment, said fulcrum joint 90 defines a first lever arm 91 and a second lever arm 92. According to an embodiment, said first lever arm 91 comprises said input portion 84. According to an embodiment, said second lever arm 92 comprises said tendon contacting portion 87.

According to an embodiment, said at least pushing device 53 comprises at least an output portion 83 and said at least one transmission device 54 comprises at least one input portion 84, said output portion 83 directly or indirectly through said sterile drape insert 73 transmitting said pushing action 75 to said input portion 84.

According to an embodiment, said output portion 83 of said pushing device 53 directly transmits said pushing action 75 to said input portion 84 of said transmission device 54. Preferably, said output portion 83 of said pushing device 53 comprises a transmitting surface 85 and said input portion 84 of said transmission device 54 comprises a transmitting counter-surface 86, said transmitting surface 85 selectively rest against said transmitting counter-surface 86 to transmit said pushing action 75 to said transmitting counter-surface 86.

According to an embodiment, said output portion 83 of said pushing device 53 indirectly transmits through said sterile barrier 55, preferably through said sterile drape insert 73, said pushing action 75 to said input portion 84 of said transmission device 54. Preferably, said output portion 83 of said pushing device 53 comprises a transmitting surface 85 and said sterile drape insert 73 comprises a transmitting counter-surface 86, said transmitting surface 85 selectively rest against said transmitting counter-surface 86 to transmit said pushing action 75 to said transmitting counter-surface 86 of said sterile drape insert 73. Preferably, said sterile drape insert 73 comprises a further transmitting surface 85 and said transmission device 54 comprise a further transmitting counter-surface 86, said further transmitting surface 85 selectively rest against said further transmitting counter-surface 86 to transmit said pushing action 75 to said further transmitting counter-surface 86 of said input portion 84 of said transmission device 54.

According to an embodiment, at least one between said at least one transmitting surface 85 and at least one transmitting counter-surface 86 is a cam. Preferably, the other between said at least one transmitting surface 85 and at least one transmitting counter-surface 86 is a follower cooperating with said cam to transmit the pushing action 75.

According to an embodiment, at least one between said at least one further transmitting surface 85 and at least one further transmitting counter-surface 86 is a cam. Preferably, the other between said at least one further transmitting surface 85 and at least one further transmitting counter-surface 86 is a follower cooperating with said cam to transmit the pushing action 75.

According to an embodiment, at least one between said at least one transmitting surface 85 and at least one transmitting counter-surface 86 comprises a working surface made of low friction material, preferably in Teflon®. According to an embodiment, at least one between said at least one transmitting surface 85 and at least one transmitting counter-surface 86 comprises a working surface made of metal, preferably polished metal to reduce friction. According to an embodiment, at least one between said at least one further transmitting surface 85 and at least one further transmitting counter-surface 86 comprises a working surface made of low friction material, preferably in Teflon®. Thanks to said low friction material said transmitting surface 85 can slide without wear onto said transmitting counter-surface 86.

According to an embodiment, said sterile barrier includes a sterile drape insert According to an embodiment, said sterile drape insert 73 is made of polymeric material, preferably in Teflon®.

According to an embodiment, said at least elastic device 56 comprises a plurality of elastic bridges 89 forming with said frame 52 and said transmission device 54 a flexural mechanism. In this way, said elastic device 56 acts as said coupling device 93 constraining said transmission device 54 to have a single degree of freedom of motion with respect to said frame 52.

According to an embodiment, said at least one elastic device 56 comprises a pair of elastic bridges 89 running parallel to each other forming with said frame 52 and said transmission device 54 a flexural mechanism. Preferably, said flexural mechanism is an flexural parallelogram. In this way, said at least one elastic device 56 acts as said coupling device constraining said transmission device 54 to have a single degree of freedom of linear motion with respect to said frame 52. Preferably, said elastic bridges 89 of said pair of elastic bridges 89 have substantially the same length. Preferably, by adjusting the length of said elastic bridges 89 is possible to modify said single degree of freedom of linear motion.

Preferably, said elastic bridges 89 deflects to exert the bias action 76 on said transmission device 54.

Preferably, each of said elastic bridges 89 is a leaf spring. Preferably, each of said elastic bridges 89 is manufactured in spring steel.

According to an embodiment, said coupling device 93 constrains said transmission device 54 to have a single degree of freedom of pivotal motion with respect to said frame 52. Preferably, said pivotal motion defines an axis of rotation Z-Z. Preferably, said pivotal motion occurs around said axis of rotation Z-Z. Preferably, said axis of rotation Z-Z is parallel to or coincident with the direction of longitudinal development of said transmission device 54.

According to an embodiment, said tendon contacting portion 87 of said at least one transmission device 54 comprises a capstan device 88 selectively winding said tendon proximal portion 26 around said tendon contacting portion 87. Preferably, said tendon contacting portion 87 is in single piece with said capstan device 88. According to an embodiment, said capstan device 88 comprises a cam portion being in contact with said tendon proximal portion 26. Preferably, said tendon termination 74 is secured to said capstan device 88.

According to an embodiment, said sterile drape insert 73 comprises frame attachment device to connect to a portion of said surgical instrument 70, and preferably to a portion of said frame 52 of said surgical instrument 70.

According to an embodiment, said sterile drape insert 73 comprises at least one first rotative coupling device 79 to connect with said at least pushing device 53. According to an embodiment, said at least one first rotative coupling device 79 comprises at least a coupling seat 78 to receive a rotative coupling portion 80 of said pushing device 53.

According to an embodiment, said sterile drape insert 73 comprises at least one second rotative coupling device 81 to connect with said at least one transmission element 54, and to transmit the pushing action 75 to said transmission device 54.

According to an embodiment, said pushing device 53 is selectively connected with said transmission device 54 and engages unidirectionally with said transmission device 54 to transmit said pushing action 75.

According to a preferred embodiment, said pushing device 53 are selectively connected with said transmission device 54 to transmit said pushing action 75 by device of a unilateral engagement between said sterile barrier 55 and said transmission device 54. In other words, said transmission device 54 avoid to transmit any pulling action on said pushing device 53.

According to an embodiment, said pushing device 53 are selectively and monolaterally connected with said transmission device 54. In this way a bilateral transmission is avoided.

Thanks to the provision of said pushing device 53 monolaterally connected to said transmission device 54, is possible to precisely control the stroke of said pushing device 53 as well as the contact force between said pushing device 53 and said transmission device 54.

According to an embodiment, said pushing device 53 directly or indirectly, through said sterile barrier 55, and releasably rest against said transmission device 54. According to an embodiment, said pushing device 53 are directly or indirectly, through said sterile barrier 55, connected to said transmission device 54 in such way to can selectively detach from said transmission device 54. In this way, the preload on said tendon 19 is maintained while said pushing device 53 selectively detach from said transmission element 54, thanks to the bias action of said elastic device 56.

According to an embodiment, said pushing device 53 are selectively connected with said sterile barrier 55 and engages unidirectionally with said sterile barrier 55 to transmit said pushing action 75. In other words, said sterile barrier 55 avoids to transmit any pulling action on said pushing device 53.

According to an embodiment, said slave manipulator 3 comprises a plurality of said pushing elements 53 and said surgical instrument 70 comprises a plurality of said transmitting elements 54. Preferably, a pushing element 53 of said plurality of pushing elements 53 is selectively connected to one transmission element 54 of said plurality of transmission elements 54.

According to an embodiment, said slave manipulator 3 comprises a plurality of said pushing elements 53 and said surgical instrument 70 comprises a plurality of said transmitting elements 54, wherein each pushing device 53 of said plurality of pushing elements 53 independently exerts said pushing action 75 on at least one respective transmission element 54. In other words, each pushing element 53 of said plurality of pushing elements 53 is movable independently from any other pushing element 53 of said plurality of pushing elements 53.

According to a preferred embodiment, said slave manipulator 3 comprises at least a second pushing device 153 working as antagonist pushing device 153. Preferably, said second pushing device or antagonist pushing device 153 works opposite with respect to the pushing device 53.

According to a preferred embodiment, said slave manipulator 3 further comprises at least a second actuator 25 connected to said antagonist pushing device 153. Preferably, said slave manipulator 3 further comprises at least second transmission device 154 working as antagonist transmission device 154. Preferably, said second transmission device 154 works opposite with respect to the transmission device 54. Preferably, said slave manipulator further comprises a second force sensor. According to an embodiment, said second sensor detects a contact force on said at least one antagonist pushing device 153. According to an embodiment, said second sensor acts as position sensing system 72.

According to a preferred embodiment, said surgical instrument 70 comprises at least a second tendon 20 working as antagonist tendons 20 and a second elastic device 156, attached to said second transmission device 154 wherein, whenever said surgical instrument 70 is attached to said slave manipulator 3, said antagonist pushing device 153 releasably and selectively connects with said antagonist transmission device 153 to transmit a pushing action to said antagonist transmission device 154 through said sterile barrier 55. Preferably said second tendons 20 works opposite with respect to said tendon 19.

Preferably, said second sensor 72 detects a contact force between said antagonist pushing device 153 and said antagonist transmission device 154. Preferably, said antagonist elastic device 156 bias said antagonist transmission device 154 away from said antagonist pushing device 153, so as to exert a traction action on said antagonist tendon 20. According to an embodiment, said tendon 19 and said antagonist tendon 20 provide opposite motion to a link 6; 7; 8; 43.

According to an embodiment, said slave manipulator 3 comprises at least a pair of pushing device 53, 153 working as antagonist pushing device 53, 153. According to an embodiment, said surgical instrument 70 comprises at least a pair of transmission device 54, 154 working as antagonist transmission device 54, 154. According to an embodiment, said surgical instrument 70 comprises at least a pair of tendons 19, 20 working as antagonist tendons 19, 20, to provide opposite motion to a link 6, 7, 8, 43. Preferably, each pushing device 53 or 153 of said pair of antagonist pushing device 53, 153 is selectively connected to the respective transmission device 54 or 154 of said pair of antagonist transmission device 54, 154 to transmit the pushing action 75 to the respective transmission device 54 or 154 in order to exert the traction action on the respective tendon 19 or 20 of said pair of antagonist tendons 19, 20 to provide opposite motion to a link 6, 7, 8, 43.

According to an embodiment, while said pair of antagonist pushing device 53, 153 are independently and releasably connected to said pair of antagonist transmission device 54, 154, said pair of antagonist tendons 19, 20 are in mechanical equilibrium and are preloaded.

According to an embodiment, said slave manipulator 3 comprises a plurality of pushing devices 53. Preferably, said plurality of pushing devices are in the exact number of six pushing devices 53.1, 53.2, 53.3, 53.4, 53.5, 53.6. Preferably, said plurality of pushing devices are in the exact number of six pushing elements 53.1, 53.2, 53.3, 53.4, 53.5, 53.6, designated to exert a pushing action on at least one transmission device 54, and preferably on respective transmission elements in number of six.

Preferably, each pushing device 53 acts along a pushing axis p-p.

Preferably, said pushing axis p-p is rectilinear.

Figure 6:
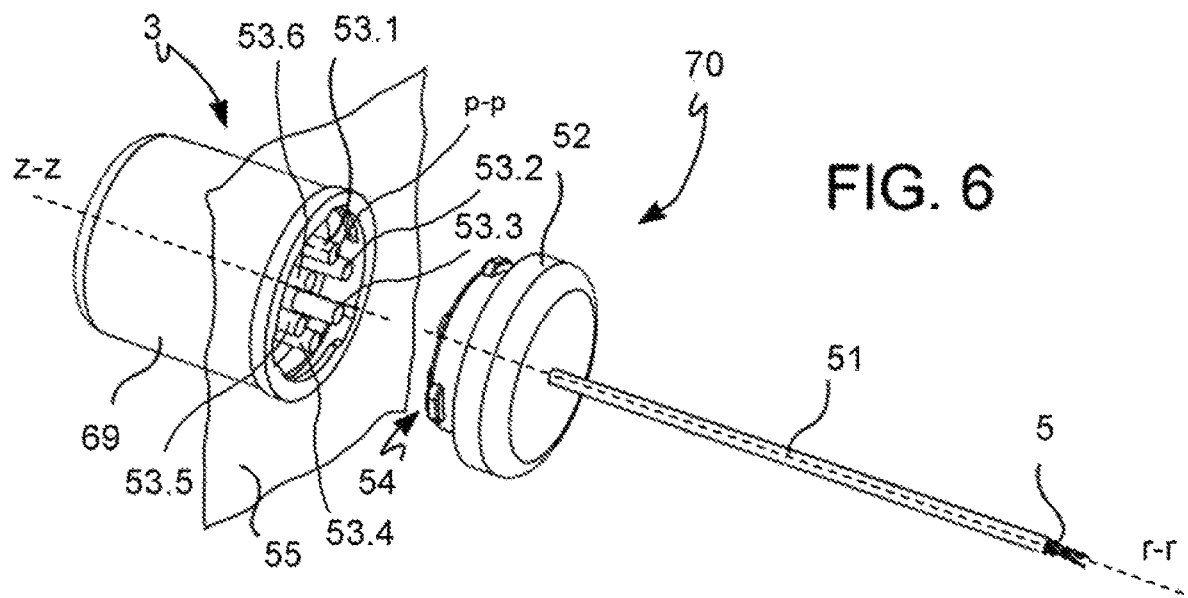
FIGS. 6 and 7 are exploded perspective views of a surgical instrument and of a slave manipulator, according to some embodiments.
Figure 7:
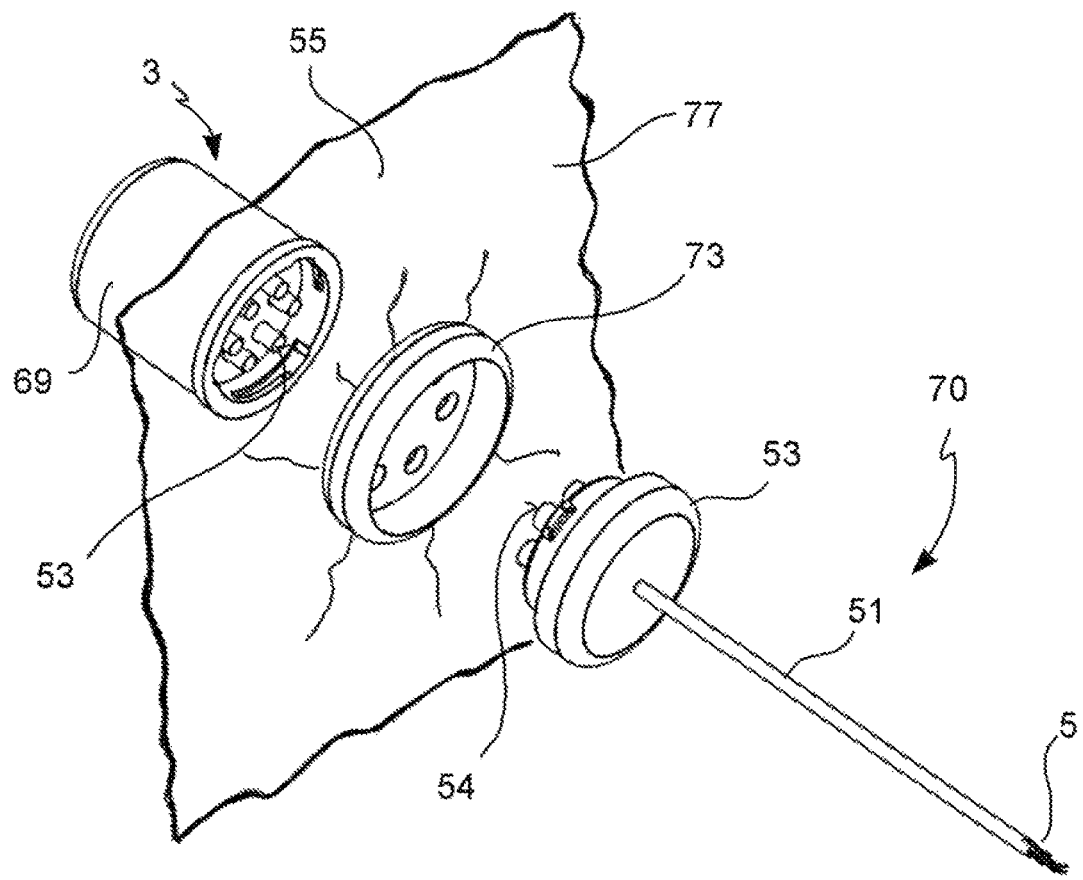
Figure 8:
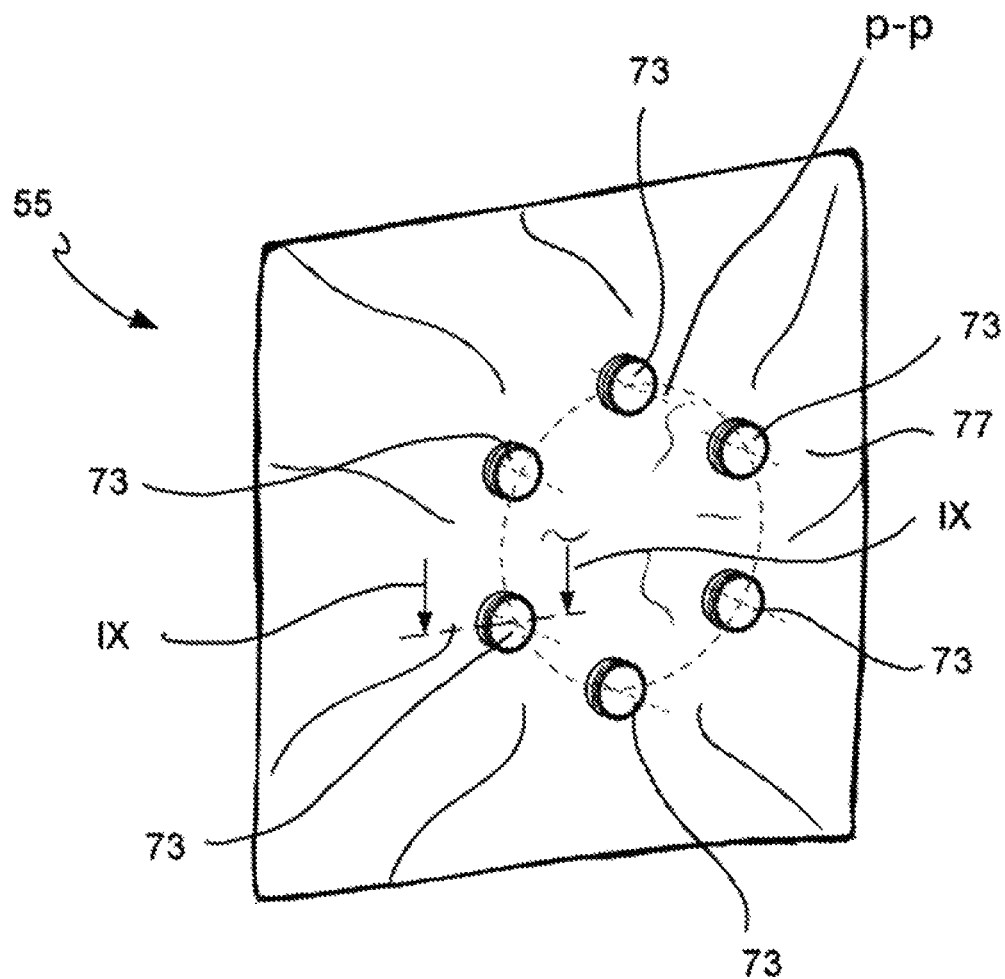
FIG. 8 is a perspective view of a sterile barrier, according to an embodiment.
Figure 9:
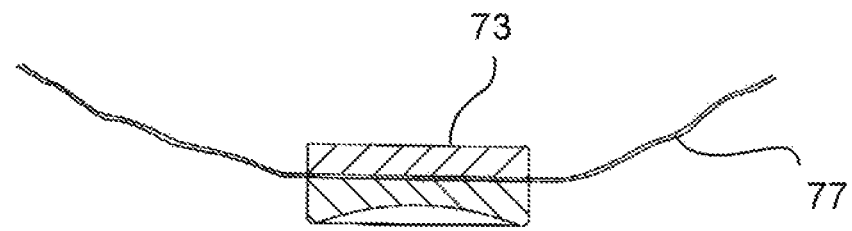
FIG. 9 is a cross-section cut along the lines indicated by the arrows IX-IX in FIG. 8.
Figure 10:
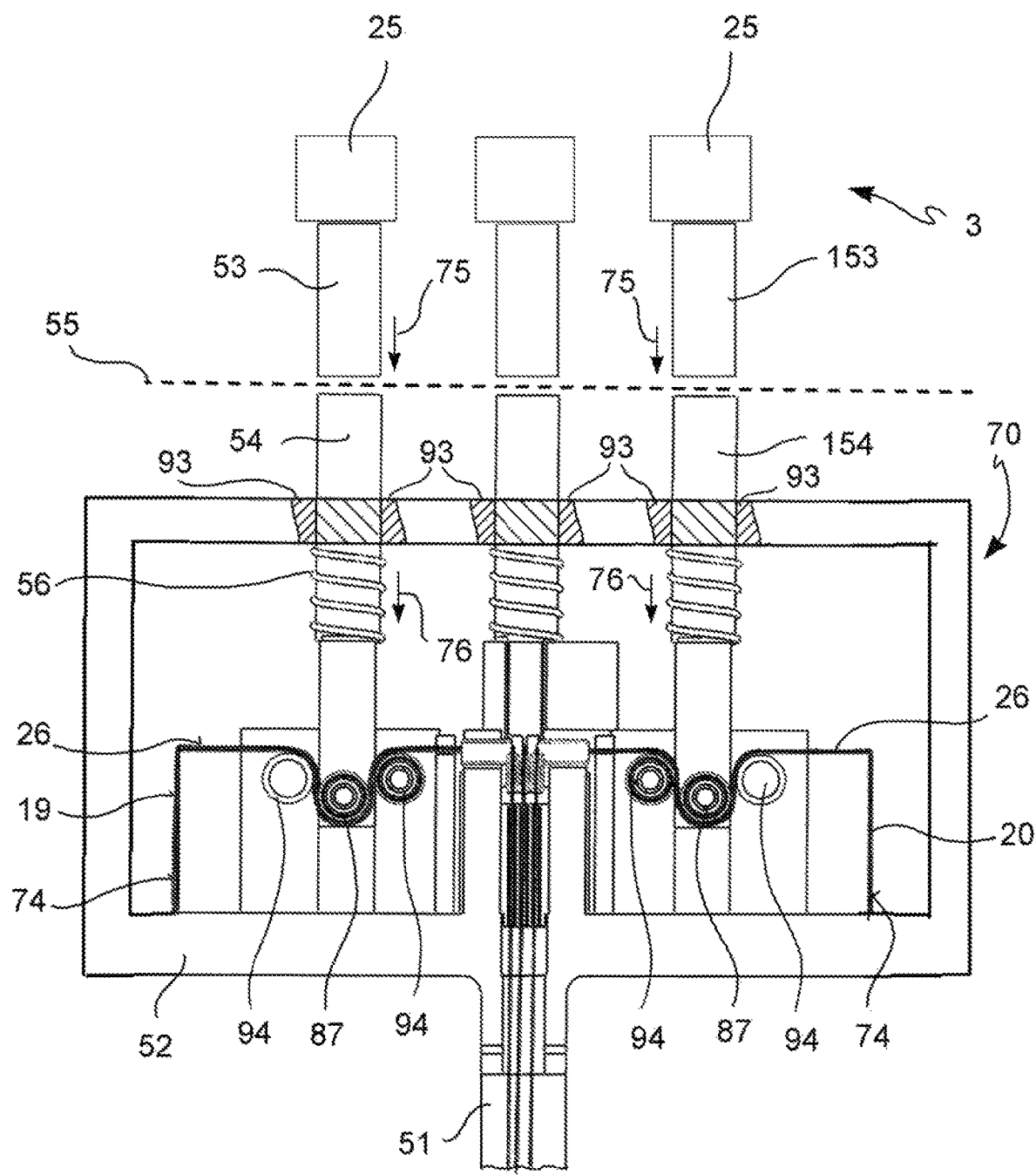
FIGS. 10 and 11 are sketches in cross-section of a of a surgical instrument and of a slave manipulator, according to some embodiments.
Figure 11:
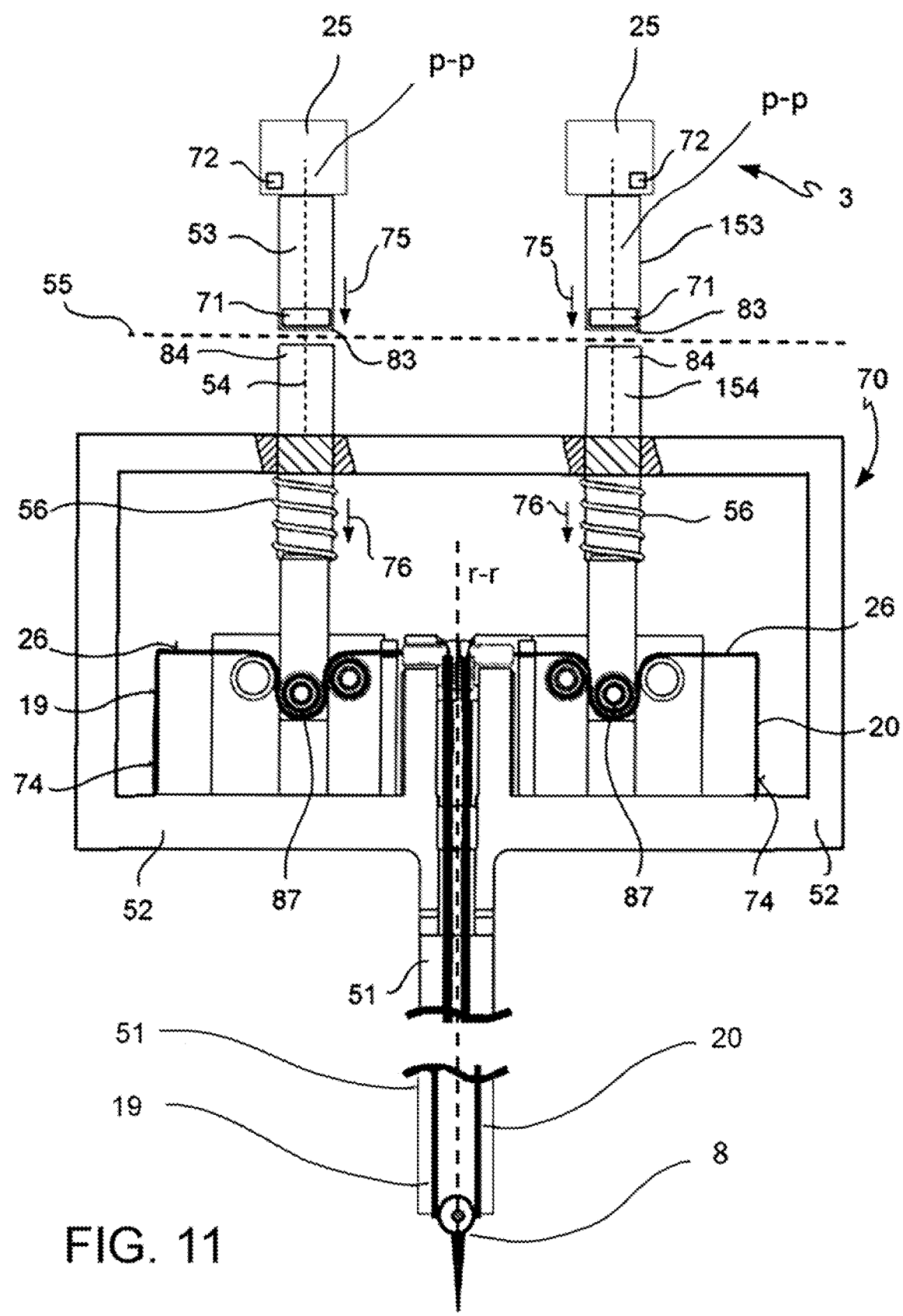
Figure 13:
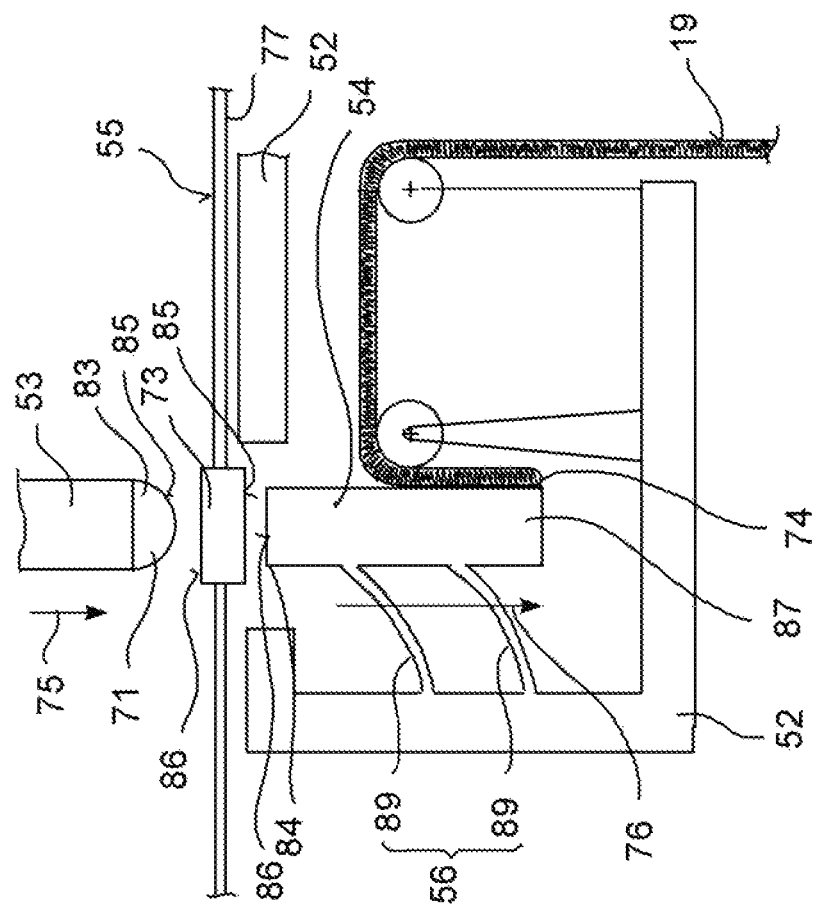
FIGS. 12 and 13 are sketches in cross-section of a of a surgical instrument and of a slave manipulator, according to some embodiments.
Figure 12:
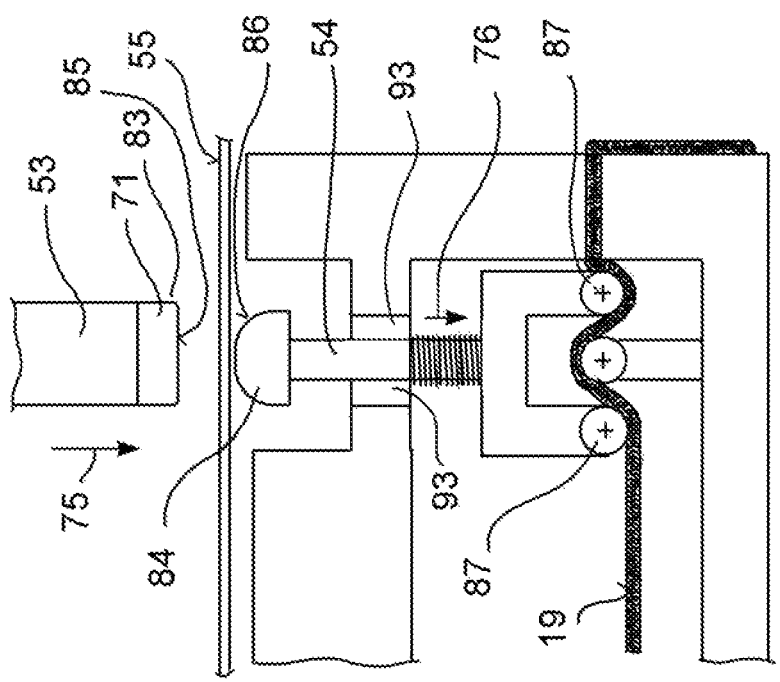
Figure 14:
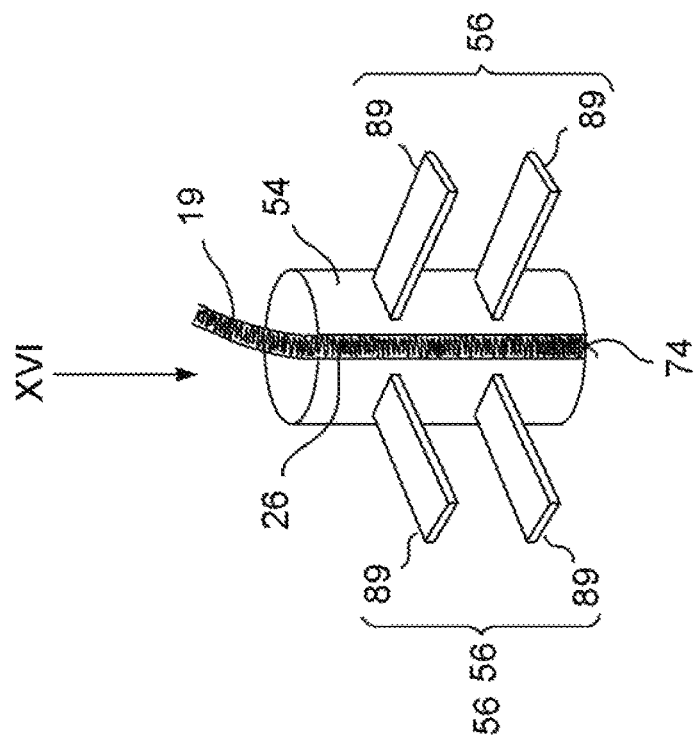
FIGS. 14 and 15 are perspective views of a transmission device, according to an embodiment, in an unbiased position and in a biased position, respectively.
Figure 15:
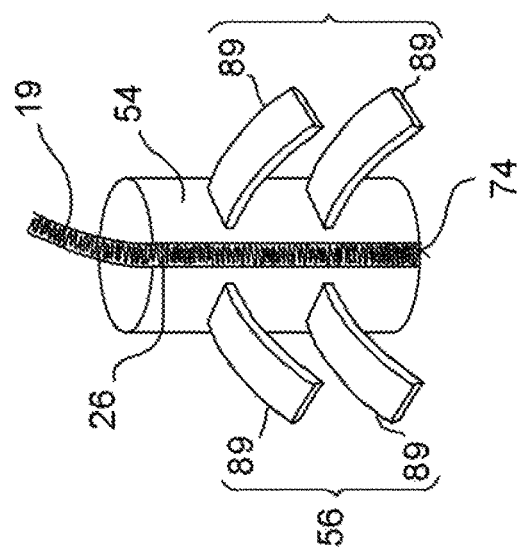
Figure 16:
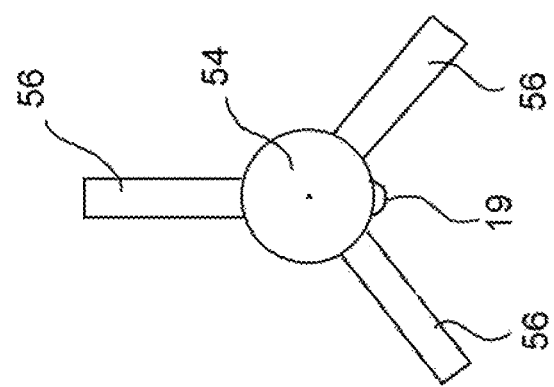
FIG. 16 is a plane view as indicated by the arrow XVI in FIG. 14.
Figure 21:
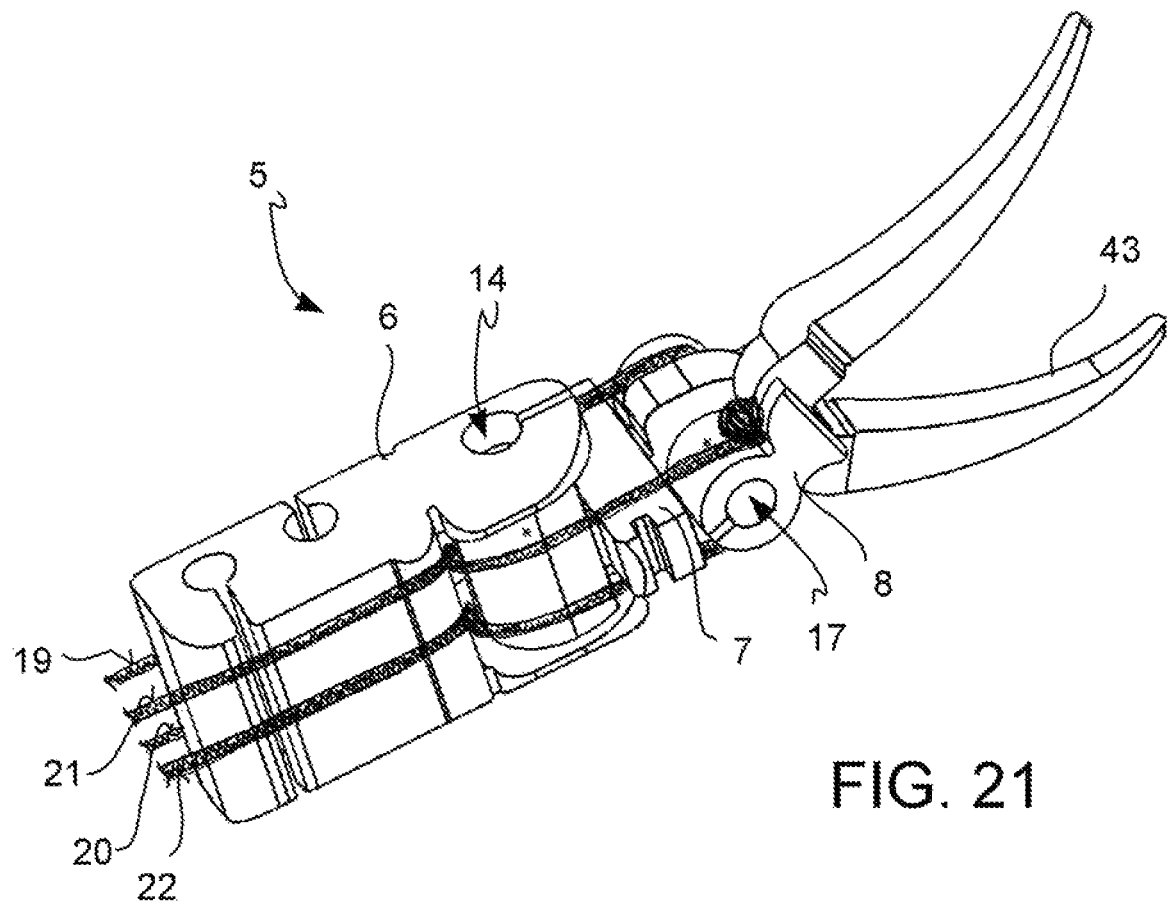
FIG. 21 is a perspective view of a jointed assembly of a surgical instrument, according to an embodiment.
Figure 22:
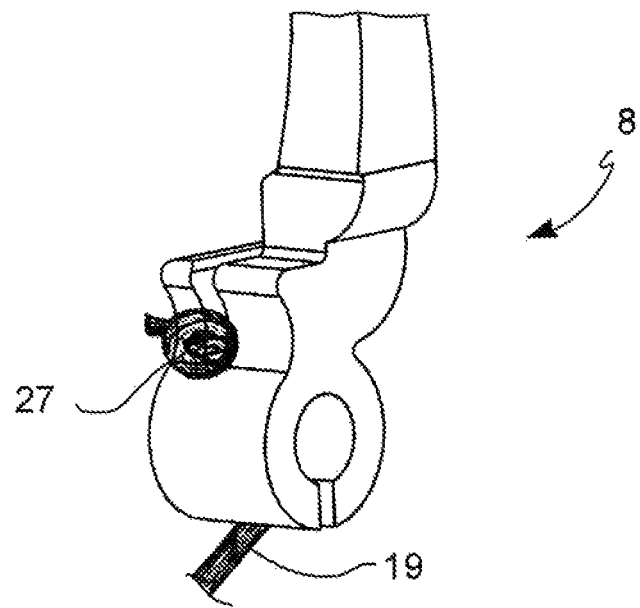
FIG. 22 is a perspective view of a portion of a link, according to an embodiment.
Figure 23:
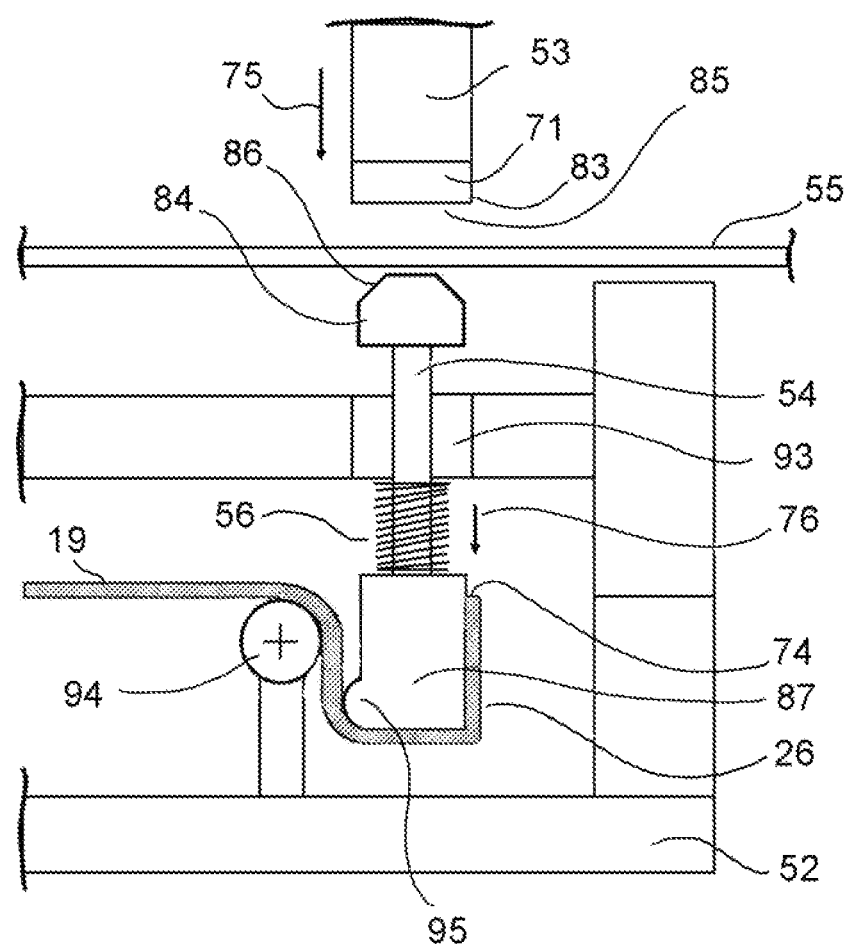
FIG. 23 is a sketch in cross-section of a surgical instrument and of a slave manipulator, according to an embodiment.

According to an embodiment, for example shown in FIG. 6, said plurality of pushing devices are in the exact number of six pushing elements 53.1, 53.2, 53.3, 53.4, 53.5, 53.6 each designed to exert a pushing action along said pushing axis p-p to a respective transmission element 54 through a respective sterile drape insert 73.

According to an embodiment, said pushing axis p-p is parallel to said longitudinal direction of shaft r-r of the shaft of the medical instruments.

According to an embodiment, said plurality of pushing elements 53.1, 53.2, 53.3, 53.4, 53.5, 53.6 are symmetrically arranged around a longitudinal axis z-z or motorbox axis z-z.

According to an embodiment, said plurality of pushing elements 53.1, 53.2, 53.3, 53.4, 53.5, 53.6 are arranged around a longitudinal axis z-z or motorbox axis z-z and are equally spaced one another along a circumferential direction, orthogonal to said motorbox axis z-z.

According to an embodiment, said motorbox 69 defines an axis of longitudinal development of the motorbox 69, or motorbox axis z-z.

Preferably, said motorbox axis z-z acts as roll axis. In other words, said medical instruments 70 is designed to roll about said motorbox axis z-z.

According to a preferred embodiment, each pushing axis p-p is parallel to said motorbox axis z-z. Preferably, all said pushing axis p-p are equally spaced from said motorbox axis z-z.

According to an embodiment, said longitudinal axis of the shaft r-r coincides with the prolongation of the motorbox axis z-z and vice versa.

According to an embodiment, said sterile barrier 55 comprises a plurality of said sterile drape inserts 73.

According to an embodiment, said at least one actuator 25 comprises a linear nut screw in line with said pushing axis p-p. According to an embodiment, said at least one actuator 25 comprises a rotative motor.

According to an embodiment, said at least one actuator 25 is located in an actuator compartment 69 portion of said slave manipulator 3 that connects to said frame 52 of said surgical instrument 70.

According to an embodiment, said first link 6 and said second link 7 are associated in a first joint 14 providing a degree of freedom between said first link 6 and said second link 7.

According to an embodiment, said second link 7 and said third link 8 are associated in a second joint 17 providing a degree of freedom between said second link 7 and said third link 8.

According to an embodiment, said surgical instrument 70 comprises at least a tendon 19 for moving a degree of freedom.

According to an embodiment, said at least one tendon 19 is suitable for moving said third link 8 in respect of at least said second link 7. According to an embodiment, said surgical instrument 70 comprises at least a pair of tendons 19, 20 for moving a degree of freedom. According to an embodiment, said pair of tendons 19, 20 is suitable for moving said third link 8 in respect of at least said second link 7.

According to an embodiment, said jointed subassembly 5 comprises a further third link 43 associated to at least said second link 8 in said second joint 17.

According to a preferred embodiment, said tendon 19 comprises a tendon proximal portion 26, suitable to be associated to at least an actuator 25 not placed in said jointed subassembly 5, a tendon distal portion 27, secured to said third link 8, and a tendon intermediate portion 28, extending between said tendon proximal portion 26 and said tendon distal portion 27.

According to an embodiment, a pair of tendons have their tendon distal portions 27 secured to a same link, so as to work as one tendon. In other words, a pair of tendons are secured to a same link so as to work in parallel as a single tendon. According to an embodiment, a pair of tendons share their tendon distal portions 27, so as to work in parallel as a single tendon. According to an embodiment, a pair of tendons working as a single tendon are in single piece. According to an embodiment, said tendons 19, 20, 21, 22, comprises a first pair of tendons 19, 20, suitable to work as a single tendon. According to an embodiment, said tendons 19, 20, 21, 22, comprises a second pair of tendons 21, 22, suitable to work as a single tendon.

According to an embodiment, said stretchable drape 77 is movable with respect of said frame 52 of the surgical instrument 70 in a direction substantially orthogonal to the main surface of said stretchable drape 77 for a predetermined displacement equal to or lower than 10 millimeters. Preferably, said main surface of said stretchable drape 77 is suitable to prevent bacteria contamination across said stretchable drape 77.

According to an embodiment, said stretchable drape 77 is stretchable for a predetermined displacement equal to or lower than 10 millimeters. According to an embodiment, said stretchable drape 77 is suitable for being stretched, when in use, for said predetermined displacement. Preferably, said main surface of said stretchable drape 77 is suitable to prevent bacteria contamination across said stretchable drape 77.

According to an embodiment, said stretchable drape 77 is stretchable and/or movable with respect of said frame 52 of the surgical instrument 70 in a direction substantially orthogonal to the main surface of said stretchable drape 77 for a predetermined displacement equal to or lower than 10 millimeters.

According to an embodiment, said stretchable drape 77 is suitable for being stretched, when in use, for said predetermined displacement. Preferably, said stretchable drape 77 is suitable for being elastically stretched, when in use, avoiding to permanently deforms, for example plastically deform.

According to an embodiment, the stroke or displacement of said transmission device 54 in respect of said frame 52 of said surgical instrument 70, when said transmission device 54 being by said pushing device 53, is equal to or lower than 10 millimeters.

According to an embodiment, the linear stroke or linear displacement of said tendon contacting portion 87 of said transmission device 54 in respect of said frame 52 of said surgical instrument 70, when said transmission device 54 being by said pushing device 53, is equal to or lower than 10 millimeters.

According to an embodiment, the pivotal stroke or pivotal displacement of said tendon contacting portion 87 of said transmission device 54 in respect of said frame 52 of said surgical instrument 70, when said transmission device 54 being by said pushing device 53, is equal to or lower than 10 millimeters. Preferably, said tendon contacting portion 87 of said transmission device 54 acts as a transmission output portion.

According to an embodiment, said transmission device 54 selectively retrieve a determined retrieved length of said tendon 19. Preferably, said determined retrieved length is equal to or lower than 10 millimeters. According to an embodiment, said transmission device 54 selectively release a determined released length of said tendon 19. Preferably, said determined released length is equal to or lower than 10 millimeters.

According to an embodiment, said bias action 76 has a value comprised between 0.1 Newton and 5 Newton. Preferably, said bias action 76 has a value comprised in range 0.1 Newton to 5.0 Newton.

According to an embodiment, said bias action 76 has a value equal to or lower than the 10% of the breaking load of said tendon. Preferably, said bias action 76 has a value equal to or lower than the 10% of the breaking load of said tendon proximal portion 26. said bias action 76 has a value equal to or lower than the 10% of the breaking load of said tendon intermediate portion 28.

According to a preferred embodiment, said tendon 19 is routed on a tendon guiding element 94 or tendon return element 94. According to a preferred embodiment, said tendon guiding element 94 is a sliding surface. According to a preferred embodiment, said tendon guiding element 94 is an idle pulley. According to a preferred embodiment, said tendon guiding element 94 is a ball bearing. Preferably, said tendon guiding element 94 is attached to said frame 52 and protrudes cantilevered to touch said tendon.

According to a preferred embodiment, said transmission countersurface 86 is a flat surface. Preferably, said transmission countersurface 86 faces a flat surface to said transmission surface 85 of the pushing device 54.

According to a preferred embodiment, said tendon 19 is secured on said transmission device 54. For example, said tendon proximal portion is glued to said tendon contacting portion 87 of said transmission device 54, for example to a plunger of said transmission device 54. Preferably each tendon proximal portion is secured to each plunger of said transmission device 54. According to a preferred embodiment, said tendon proximal portion 26 is secured on said transmission device 54.

According to a preferred embodiment, said tendon contacting portion 87 is a protrusion surface 95 to avoid tendon wear and friction against said transmission device 54 while in motion. According to an embodiment, said protrusion surface 95 protrudes from said frame 52 to touch said tendon.

According to a preferred embodiment, said coupling device 93 constrains said transmission device 54 to have a single degree of freedom of linear motion with respect to said frame 52.

According to a preferred embodiment, said coupling device 93 is a bush or a linear bearing. According to a preferred embodiment, said linear bearing can hold torsion moment created by off axis forces while guaranteeing low friction in axis linear motion.

According to an embodiment, said tendon contacting portion 87 of the transmission device 54 comprises at least one protrusion 95, preferably dome-shaped, in contact with a portion of the tendon proximal portion 26. Preferably, said tendon proximal portion 26 is returned around a curved surface of the protrusion 95, for example a curved surface protruding towards the elastic device. Preferably, the tendon proximal portion 26 is firmly attached to said tendon contacting portion 87. Preferably, said elastic device 56 biases said tendon contacting portion 87 away from the curved surface protruding towards the elastic device which returns said tendon proximal portion.

According to a general embodiment, it is provided a surgical instrument 70 according to any one of the embodiments previously described.

According to a general embodiment, it is provided a slave assembly comprising at least a slave manipulator 3, according to any one of the embodiments previously described, and at least a surgical instrument 70, according to any one of the embodiments previously described.

It follows a description of a method for controlling a surgical instrument 70.

According to a general embodiment, a method for controlling a surgical instrument 70 attached to a slave manipulator 3, according comprising the following steps:
- -a- compute or receive an actuator position increment command;
- -b- read or detect from said sensor 71, 72 a contact force value on said pushing device 53;
- -c- compare said contact force value with a force threshold to detect contact between said pushing device 53 and said transmission device 54;
- -d- if force value is equal or above said first force threshold,
  then command said actuator 25 to advance of said actuator position increment command;
- -e- if said force value is below a first force threshold,
  then command an actuator to advance until said force value is above said first force threshold, or until a maximum actuator position increment is reached, and store total actuator position correction.

According to a preferred operating method, said phase -d- and -e- are performed alternatively.

According to a preferred operating mode, the method allows to control the action of said actuator with feedback on the position of the actuator.

According to a preferred operating mode, the method evaluates the contact force value detected by said sensor 71, 72 in respect of a predefined first threshold value, and perform either one of the following step: if the detected force value is equal or above said first force threshold, then command said actuator 25 to advance of said actuator position increment command; or if said force value is below a first force threshold, then command an actuator to advance until said force value is above said first force threshold, or until a maximum actuator position increment is reached, and store total actuator position correction.

According to a possible operating mode, said steps from -a- to -c- are preformed in succession following the order described above. According to a possible operating mode, said steps from -c- to -d- are preformed in succession following the order described above. According to a possible operating mode, said steps from -c- to -e- are preformed in succession following the order described above.

According to an operating mode, said method for controlling a surgical instrument 70 comprises at least one, but also all, of the following further steps:

-f- command an actuator 25 to move to a retracted home position;
-g- store an initial actuator position;
-h- attach a surgical instrument 70 to a slave manipulator 3;
-i- read from said sensor 71, 72 a force value on said pushing device 53;
-j- command said actuator 25 to advance while aid force value is below a first force threshold that indicates that contact between said pushing device and said transmission device is established;
-k- store a final actuator position;
-l- compute an instrument home position including a difference between said final actuator position and said initial actuator position.

According to a preferred operating mode, said steps from -f- to -l- are all performed before said step -a-.

According to a preferred operating mode, at least one of said steps from -f- to -l- is performed before said step -a-.

According to a possible operating mode, after a surgical instrument 70 is attached to said slave manipulator 3, an actuator of said slave manipulator is positioned in contact with a transmission element of said surgical instrument 70, so as to be ready to apply a force greater that a force threshold value to said transmission element 54. According to said method, after a surgical instrument is attached to said slave manipulator, an actuator is positioned in contact with the transmission element 54, independently of the position of the transmission element 54.

The cooperation of said method and said elastic device 56 guarantee that according to said method, an actuator 25 is positioned in contact with the transmission element 54, so as to be ready to exert traction on said tendon 19.

According to an operating mode, said method for controlling a surgical instrument 70 comprises the step of providing a robotic surgical assembly 1 according to any one of the embodiments previously described.

According to a possible operating mode, an actuator advances 25 of a total actuator position correction in response to slack or stretch in said tendon 19, so that an actuator position increment command is always executed starting from a actuator position such that said pushing device 53 are in contact with said transmission device 54.

Thanks to said method, an actuator position increment command leads to an associated joint motion without any motion lost due to tendon slack or stretch.

According to an operating mode, said method comprises the following step of storing the information about the position of the pushing device 53 when said contact force is detected. Preferably, said step is performed by said sensor 72 or said position sensing system 72.

According to an operating mode, said method comprises the following step of determining the position of the pushing device 53 in respect of a predefined reference position, when said contact force is detected. Preferably, said step is performed by said control unit 4.

According to an operating mode, said method comprises the following step of determining the length of the free stroke of said pushing device 53.

According to an operating mode, said method comprises the following step of determining the position of the transmission device 54 in respect of a predefined reference position, when said contact force is detected. Preferably, said step is performed by said control unit 4.

By virtue of the features described above, provided either separately or in combination, where applicable, in particular embodiments, it is possible to satisfy the sometimes contrasting needs disclosed above, and to obtain the aforesaid advantages, and in particular:

it is provided a miniaturization of a surgical instrument;
when the instrument is detached from the master—slave system, the tendons in the instrument keep a positive tension and the pretensioning element takes up any slack in the tendon, as slack in the tendons can result from the repositioning of the distal articulated subassembly members on which the tendons are distally connected;
it is provided a tendon drive system that avoids slack in a tendon permits to route the tendons over guiding members that do not capture the tendons, by employing the pretension in the cable to keep the tendons in place over the guiding members.
it is provided a tendon drive system that avoids slack in a tendon and therefore permits to route a tendon over mechanical transmission device such as pulleys, pins, link members keeping a stable tendon path.
it is provided a tendon drive system that avoids slack in the tendon and thus permits to avoid guiding tendons in sheaths, such as Bowden cables, that introduce additional friction;
it is provided a tendon drive system that avoids slack in a tendon and therefore permits to make use of tendons that are prone to creep or stretch under a load tension such as polymeric tendons;
it is provided a tendon drive system that avoids slack in a tendon and thus permits to immediately transmit motion to a distal articulated assembly without requiring an intermediate action to pick up slack in a tendon;
it is provided a master slave system for driving a medical instrument adapted to provide a sterile barrier between the medical instrument and the master slave system, said sterile barrier is a continuous sheet without holes to better prevent contamination across the sterile barrier;
it is provided a tendon drive system for a medical instrument including a distal articulated subassembly that comprises a transmission device adapted to transmit forces from an actuator of a master slave system to said tendon, wherein said transmission device is further adapted to connect to said actuator through a sterile barrier;
it is provided a tendon drive system for a medical instrument including a distal articulated subassembly that comprises a tendon tensioning element, for example an elastic element, that is mechanically in parallel with a transmission device adapted to transmit forces from an actuator of a master slave system to said tendon;

it is provided a tensioning element that provides tension on the tendon only when the actuator is not acting on the tendon and that is excluded from the force transmission path from the actuator to the tendon then the actuator is acting on the tendon;

by providing a tensioning element that is excluded from the force transmission path from the actuator to the tendon then the actuator is acting on the tendon, the stiffness of the force transmission path from the actuator to the tendon is not reduced as a result of the intervening compliance of the tensioning element;

by avoiding a reduced stiffness of the force transmission path from the actuator to the tendon allows to improves the precision of the motion of the distal articulated subassembly by overcoming friction effects in a distal articulated subassembly with a stiffer drive train;

it is provided, in a master slave system for driving a medical instrument, a transmission device adapted to engage unidirectionally with an actuator;

advantageously, such unidirectional connection between an actuator and an instrument transmission device has the advantage to allow to employ a simple continuous sterile barrier, much like a loose drape trapped between the actuator and the transmission device, avoiding the use of a sterile barrier with holes and moving parts;

advantageously, the cooperation of a unidirectional connection between an actuator and an instrument transmission device with a tensioning element in parallel with said transmission device has the distinctive advantage of allowing slack in the tendon to be picked up by the tensioning element without requiring an immediate action from the actuator, thus simplifying the control of the actuator and its actuator response time requirements;

further, a unidirectional connection between an actuator and an instrument transmission device that a transmission device that is not connected bidirectionally with the actuator; in other words, the actuator applies a force action on said transmission device when moving in a first direction while in contact with said transmission device and release force on said transmission device when moving in a second direction opposite to said first direction while in contact with aid transmission device.

the lack of a bidirectional connection device that by moving in said second opposite direction, the actuator can completely release contact with said transmission device;

furthermore, the lack of a bidirectional connection, and the cooperation of said tensioning element in parallel with said transmission device, device that said transmission device release contact with said actuator to pick up slack in the tendon for instance a slack resulting from the repositioning of the distal articulated subassembly members on which the tendons are distally connected;

it is provided a sensing system that can sense the force exchanged between the actuator and the transmission device in the medical instrument across a sterile barrier and transmit a force information related to the tendon tension to a processor in the master slave system that controls the motion of an actuator;

the cooperation of a force sensing system collecting information directly related the tendon tension with a processor that controls the motion of an actuator allows the processor to command an immediate action to the actuator to pick up slack in the tendon, for instance a slack resulting from the repositioning of the distal articulated subassembly elements on which the tendons are distally connected.

Those skilled in art may make many changes and adaptations to the embodiments described above or may replace elements with others which are functionally equivalent in order to satisfy contingent needs without however departing from the scope of the appended claims.

LIST OF REFERENCES

1 Robotic microsurgery assembly
2 Master tool
3 Slave or slave manipulator
4 Control unit
5 Jointed subassembly
6 First link
7 Second link
8 Third link
14 First joint
17 Second joint
19 Tendon
20 Antagonist tendon
21, 22 Second pair of tendons
25 Actuator
26 Tendon proximal portion
27 Tendon distal portion
28 Tendon intermediate portion
29 Patient
30 Surgeon
43 Further third link
51 Shaft
52 Frame
53 Pushing device
53.1, 53.2, 53.3, 53.4, 53.5, 53.6 pushing elements of the pushing device
54 Transmission device
55 Sterile barrier
56 Elastic device or elastic device
58 Actuator drive unit
59 First command signal
60 Second command signal
61 Tubular element connection
69 Motor box or motor compartment
70 Medical Instrument or surgical instrument or instrument
71 Sensor
72 Position sensing system
73 Sterile drape insert
74 Tendon termination
75 Pushing action
76 Bias action
77 Stretchable drape of the sterile barrier
78 Rotative coupling seat
79 First rotative coupling device
80 Rotative coupling portion
81 Second rotative coupling portion
83 Output portion of the pushing device
84 Input portion of the transmission device
85 Transmitting surface
86 Transmitting countersurface
87 Tendon contacting portion
88 Capstan portion
89 Flexural element or elastic bridge of the elastic device
90 Fulcrum joint
91 First lever arm
92 Second lever arm 93 Coupling device
94 Tendon return element or tendon guiding element
95 Protrusion surface
153 Antagonist pushing device
154 Antagonist transmission device
156 Antagonist elastic device
p-p Pushing direction or pushing axis
z-z Motorbox axis or axis of longitudinal development of the motorbox
Z-Z Axis of rotation
r-r Longitudinal direction of the shaft

The invention claimed is:
1. A robotic surgical assembly comprising:
a slave manipulator comprising:
an actuator;
at least one pushing device, connected to said actuator;
at least one sensor detecting a contact force on said pushing device;
a position sensing system;
a sterile barrier;
at least one control unit configured to receive information about said sensor to control said actuator;
a surgical instrument operated by said slave manipulator and detachably attached to said slave manipulator and separated from said slave manipulator by said sterile barrier; said surgical instrument comprising:
a frame;
a link articulating in a joint with respect to said frame;
a tendon, associated with said actuator, having a tendon proximal portion, and a tendon distal portion, secured to said link;
at least one transmission device, in contact with said tendon proximal portion to exert a traction action on said tendon; said transmission device being constrained by a coupling device to have a single degree of freedom of motion with respect to said frame;
at least one elastic device attached between said instrument frame and said transmission device; and
wherein, when said surgical instrument is attached to said slave manipulator:
said at least one pushing device releasably and selectively connects with said transmission device to transmit a pushing action to said transmission device through said sterile barrier;
said at least one sensor detects a contact force between said pushing device and said transmission device;
said at least one elastic device biases said at least one transmission device away from said pushing device, to exert a traction action on said tendon.

2. The robotic surgical assembly according to claim 1, wherein said slave manipulator comprises:
at least a second pushing device working as an antagonist pushing device;
at least a second actuator connected to said antagonist pushing device;
at least second transmission device working as an antagonist transmission device;
a second force sensor;
wherein said surgical instrument comprises at least a second tendon working as antagonist tendons and a second elastic device, attached to said second transmission device wherein, whenever said surgical instrument is attached to said slave manipulator, said antagonist pushing device releasably and selectively connects with said antagonist transmission device to transmit a pushing action to said antagonist transmission device through said sterile barrier; and/or
wherein said second sensor detects a contact force between said antagonist pushing device and said antagonist transmission device; and/or
wherein said antagonist elastic device biases said antagonist transmission device away from said antagonist pushing device, so as to exert a traction action on said antagonist tendon;
and/or wherein said tendon and said antagonist tendon provide opposite motion to a link.

3. The robotic surgical assembly according to claim 1, wherein said pushing device selectively connects with at least one transmission device to transmit said pushing action by said pushing device of a unilateral engagement between said sterile barrier and said transmission device.

4. The robotic surgical assembly according to claim 1, wherein said sterile barrier comprises a stretchable sterile drape and when said pushing device connects to said transmission device to transmit said pushing action, a portion of said stretchable sterile drape is trapped between said pushing device and said transmission device.

5. The robotic surgical assembly according to claim 1, wherein said sterile barrier comprises a stretchable sterile drape and a sterile drape insert, attached to said drape, wherein when said pushing device connects to said transmission device to transmit said pushing action, said sterile drape insert is trapped between said pushing device and said transmission device.

6. The robotic surgical assembly according to claim 1, wherein:
said coupling device constrains one of said transmission device to have a single degree of freedom of linear motion with respect to said frame; and/or
said elastic device comprise an axial spring.

7. The robotic surgical assembly according to claim 1, wherein:
said coupling device constrains said transmission device to have a single degree of freedom of pivotal motion with respect to said frame; and/or
said elastic device comprise a torsion spring.

8. The robotic surgical assembly according to claim 1, wherein said at least one transmission device comprises at least one of:
a cam surface;
a ball bearing;
a lever pivotally connected to said frame;
a plunger;
a tendon attachment surface.

9. The robotic surgical assembly according to claim 1, wherein said elastic device and/or said coupling device comprises a plurality of flexural elements, extending from said frame to said transmission device.

10. The robotic surgical assembly according to claim 1, wherein said stretchable drape is stretchable and/or movable with respect to said frame of the surgical instrument in a direction substantially orthogonal to the main surface of said stretchable drape for a predetermined displacement equal to or lower than 10 millimeters.

11. The robotic surgical assembly according to claim 1, wherein said transmission device urges said tendon proximal portion transversally, to generate a traction action onto said intermediate portion of said tendon; and/or
wherein said tendon contacting portion of said transmission device pushes said tendon proximal portion in a direction transverse to the local longitudinal development of said tendon, so that a transversally-directed action applied to said tendon by said pushing device through said transmission device generates a traction action onto at least said intermediate portion of said tendon; and/or wherein said actuator advances a total actuator position correction in response to slack or stretch in said tendon, so that an actuator position increment command is always executed starting from an actuator position so that said pushing device is in contact with said transmission device.

12. A method for controlling the robotic surgical assembly of claim 1 that is attached to the slave manipulator, according comprising the following steps:

computing or receiving an actuator position increment command;

reading from said sensor a contact force value on said pushing device;

comparing said contact force value with a force threshold to detect contact between said pushing device and said transmission device;

wherein if said force value is equal or above said first force threshold:

commanding said actuator to advance of said actuator position increment command; and wherein if said force value is below a first force threshold:

commanding the actuator to advance until said force value is above said first force threshold, or until a maximum actuator position increment is reached, and storing total actuator position correction.

13. The method according to claim 12, comprising the following further steps, before said step of computing or receiving:

commanding the actuator to move to a retracted home position;

storing an initial actuator position;

attaching the surgical instrument to the slave manipulator;

reading from said sensor a force value on said pushing device;

commanding said actuator to advance while said force value is below a first force threshold indicating contact between said pushing device and said transmission device is established;

storing a final actuator position;

computing an instrument home position including a difference between said final actuator position and said initial actuator position.

* * * * *